United States Patent
Bales et al.

(10) Patent No.: US 8,623,070 B2
(45) Date of Patent: Jan. 7, 2014

(54) TAPERED HELICAL STENT AND METHOD FOR MANUFACTURING THE STENT

(76) Inventors: Thomas O. Bales, Coral Gables, FL (US); Charles Slater, Fort Lauderdale, FL (US); Scott Jahrmarkt, Miami Beach, FL (US)

( * ) Notice: Subject to any disclaimer, the term of this patent is extended or adjusted under 35 U.S.C. 154(b) by 1635 days.

(21) Appl. No.: 11/715,859

(22) Filed: Mar. 8, 2007

(65) Prior Publication Data
US 2008/0221664 A1    Sep. 11, 2008

(51) Int. Cl.
*A61F 2/06*    (2013.01)

(52) U.S. Cl.
USPC ........................................... 623/1.22

(58) Field of Classification Search
USPC ............ 623/1.22, 1.15, 1.3, 1.31, 1.37, 1.13, 623/1.17–1.21, 1.35; 606/108, 194
See application file for complete search history.

(56) References Cited

U.S. PATENT DOCUMENTS

| | | | |
|---|---|---|---|
| 5,061,275 A | 10/1991 | Wallsten et al. | |
| 5,741,333 A | 4/1998 | Frid | |
| 5,824,040 A | 10/1998 | Cox et al. | |
| 5,876,432 A | 3/1999 | Lau et al. | |
| 5,913,897 A | 6/1999 | Corso, Jr. et al. | |
| 5,922,021 A | 7/1999 | Jang | |
| 5,938,697 A | 8/1999 | Killion et al. | |
| 6,013,854 A | 1/2000 | Moriuchi | |
| 6,042,597 A | 3/2000 | Kveen et al. | |
| 6,159,238 A | 12/2000 | Killion et al. | |
| 6,165,210 A | 12/2000 | Lau et al. | |
| 6,355,059 B1 | 3/2002 | Richter | |
| 6,423,091 B1 * | 7/2002 | Hojeibane | 623/1.15 |
| 6,540,777 B2 | 4/2003 | Stenzel | |
| 6,569,193 B1 | 5/2003 | Cox et al. | |
| 6,652,576 B1 | 11/2003 | Stalker | |
| 6,896,696 B2 | 5/2005 | Doran et al. | |
| 7,070,617 B2 | 7/2006 | Kula | |
| 2004/0034402 A1 | 2/2004 | Bales et al. | |
| 2004/0106985 A1 * | 6/2004 | Jang | 623/1.16 |

FOREIGN PATENT DOCUMENTS

| | | |
|---|---|---|
| EP | 1059894 | 7/2005 |
| WO | 9834668 | 8/1998 |
| WO | 9853759 | 12/1998 |
| WO | 0189421 | 11/2001 |

* cited by examiner

*Primary Examiner* — Ryan Severson
*Assistant Examiner* — Tin Nguyen
(74) *Attorney, Agent, or Firm* — Mayback & Hoffman, P.A.; Gregory L. Mayback

(57) ABSTRACT

A tapered helical implantation device for peripheral arteries and other body lumina of locally varying diameter, including struts connected by loops and shaped in a helical winding. The helical winding defines turns and, when expanded, has a first end with a first expanded circumference and a second end with a second expanded circumference greater than the first expanded circumference to form a stent tapering outward from the first end towards the second end. Bridges connect adjacent ones of the turns. The struts, the loops, and the bridges define a series of pores aligned along the helix, the pores having a substantially uniform pore size. The pores has a substantially similar area. The pore size limits a size of a particle that can pass therethrough. In particular, the pore size limits a size of a spherical particle that can pass therethrough.

38 Claims, 17 Drawing Sheets

FIG. 7    Prior Art
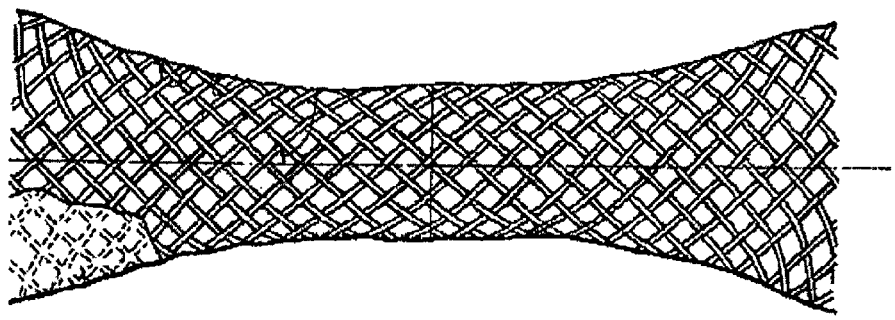
Prior Art    FIG. 8        FIG. 9    Prior Art
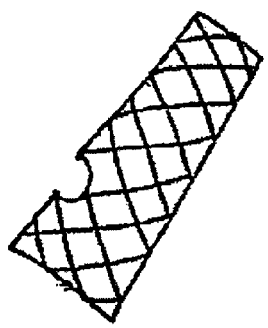      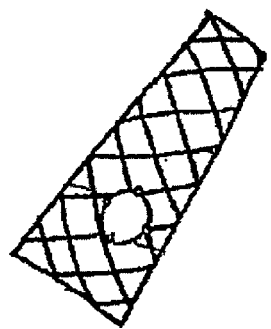
Lateral view            Frontal view FIG. 10
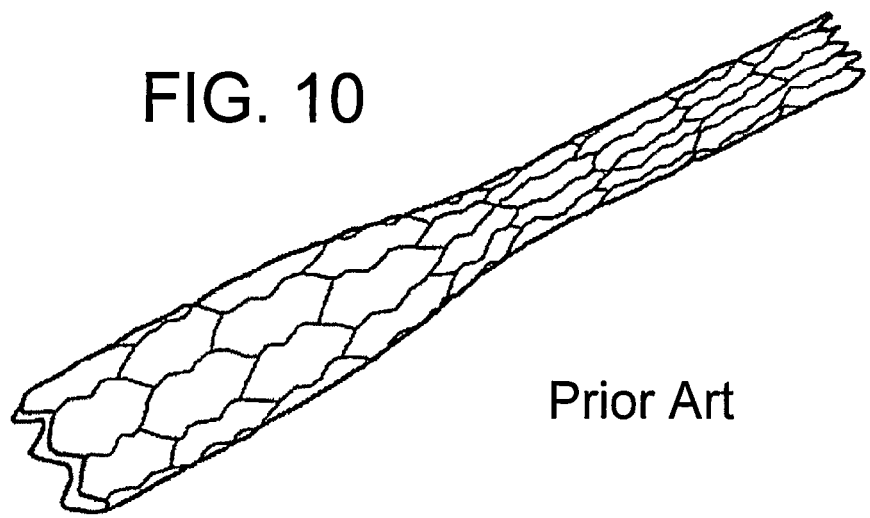
Prior Art
FIG. 11
Prior Art
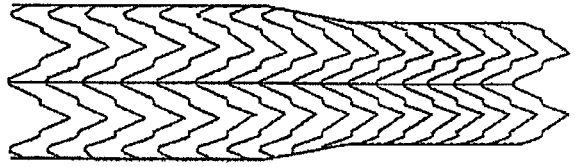
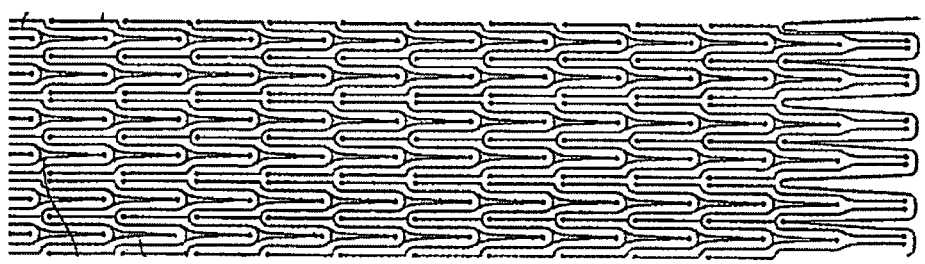
FIG. 12
Prior Art

TAPERED HELICAL STENT AND METHOD FOR MANUFACTURING THE STENT

BACKGROUND OF THE INVENTION

Field of the Invention

The present invention relates to vascular stents. In particular, the invention relates to tapered helical stents for peripheral arteries and other body lumina of locally varying diameter, e.g., the carotid artery.

Stents are used in various lumina of the body, including the biliary tree, the venous system, peripheral arteries, and coronary arteries. Stents open or hold open a lumen that has been blocked (occluded) or reduced in size (stenosed) by some disease process, such as atherosclerosis or cancer. Previously developed stents for use in the biliary, venous, and arterial systems have been of two broad classes: balloon-expanded and self-expanding. In both of these classes, stents have been made by different techniques, including forming from wire and machining from a hollow tube; such machining may be done by photo-chemical etching, laser-cutting, stamping, piercing, or other material-removal processes. Other manufacturing techniques have been proposed, such as vacuum or chemical deposition of material or forming a tube of machined flat material, but those "exotic" methods have not been widely commercialized.

The vast majority of stents for use in the arterial and venous systems have been made by machining (typically, laser machining) a pattern of struts and connecting elements from a metallic tubular pre-form. Of these machined-tube stents, there have been two basic architectures: circumferential and helical. Circumferential configurations are based upon a series of cylindrical bands joined longitudinally by bridges to make a tubular structure. Helical configurations include a continuous helical structure (typically made of a string of cells or an undulating pattern of struts and end-loops) with joining structures (referred to below as "bridges") joining adjacent turns of the helix to provide mechanical integrity to the tubular structure (to prevent unwinding, kinking, and buckling). As used herein, "struts" are lengthwise elements aligned either along the axis of a stent or perpendicular to the axis of the helical winding. Struts are connected to one another by 180-degree connector curves, referred to herein as "loops". Between adjacent turns of a helical winding, are the "bridges," which join loops of one turn to nearby loops of an adjacent winding.

Prior art helical stents are discussed in various patents and publications. An exemplary set of such helical stents include United States Patent Publication No. 2002/0116044 to Cottone et al. (corresponding to International Publication no. WO 01/89421), and U.S. Pat. No. 6,423,091 to Hojeibane, U.S. Pat. No. 5,913,897 to Corso (forms stent with helically-wound serpentine wire shown in FIG. 1), U.S. Pat. No. 6,042,597 to Kveen (forms stent by machining a tube shown in FIG. 2), U.S. Pat. No. 6,013,854 to Moriuchi (helical stent formed of angle-shaped repeating wire units as set forth in FIG. 3), U.S. Pat. No. 5,922,021 to Jang (balloon-expanded tapered stent as shown in FIG. 4), U.S. Pat. No. 5,938,697 to Killion (stent having different diameters as shown in FIG. 5), U.S. Pat. No. 5,061,275 to Wallsten (self-expanding prosthesis made by braiding individual elastic metal wires shown in FIG. 6), U.S. Pat. No. 5,741,333 to Frid (self-expanding stent constructed by plaiting elastic metal wires as shown in FIG. 7), U.S. Pat. No. 6,652,576 to Stalker (variable stiffness stent from heat treating), International Publication Nos. WO 98/53759 to Yadav (carotid stent formed from braided individual elastic wires shown in FIGS. 8 and 9) and WO 98/34668 to Roubin et al. (corresponding to United States Patent Publication Nos. 2004/0267350A1 and 2003/0055490A1 and to U.S. Pat. Nos. 6,764,506 B2, 6,475,236 B1, 6,106,548 A, and 5,827,321 A; stent made from a tube by laser machining as shown in FIG. 10), and U.S. Pat. No. 6,569,193 to Cox (tapered self-expanding stent with varying outward pressure as shown in FIGS. 11 and 12)

Use of Self-expanding Stents in Carotids and Other Tapered Locations

Certain locations in the body have non-uniform diameters in their natural, un-diseased state. For example, the carotid artery tapers abruptly from a typical diameter of six to eight mm to a diameter of four to six mm over a short length where the common carotid artery branches to the internal carotid artery, an area which is a common site for atherosclerotic disease. See, e.g., FIG. 13. Other locations, such as the common bile duct and the location where the iliac artery joins the superficial femoral artery, have sharply-tapered segments. When a physician wishes to implant a stent in such a naturally tapered location or in a location where disease processes have caused a sharp taper that is not resolvable by angioplasty, it may be desirable to use a tapered stent so that the stent does not apply inappropriately high forces to the smaller-diameter portion of the vessel, duct, or other body lumen.

The technique of stenting a tapered location varies, depending upon whether a self-expanding or balloon-expandable stent will be implanted. To implant a balloon-expandable stent in a tapered location, it is necessary to use a tapered balloon or to progressively dilate the vessel along its length; typically, a non-tapered stent (one having uniform size and properties along its length) is used and it is dilated more in the larger-diameter portion of the lumen to be stented. However, in such a situation, it may be advantageous to use a stent having different properties along its length, so that the desired relationship of stent to lumen may be maintained over the length of the stented region, even though the diameter varies. In particular, it may be advantageous to use a stent that, when expanded to the desired tapered shape, has uniform stiffness, flexibility, metal coverage, opening size, or other properties; only by making a stent with varying geometry or properties along its length may this result be achieved.

Deployment Considerations

If a self-expanding stent is to be utilized in a tapered lumen, it is advantageous for the stent to be sized appropriately for the local diameter at each point in the lumen to be stented. For example, as shown in FIG. 13, the common carotid artery might be 7 mm in diameter, while the internal carotid artery might taper to 5 mm in diameter. Accordingly, a stent introduced from the common carotid artery (as is the common practice) should have a proximal fully-expanded diameter of 8 mm and a distal fully-expanded diameter of 6 mm, using the common practice of applying a stent which has a fully-expanded diameter slightly larger than the lumen to be treated. In addition to providing a stent of the proper fully-expanded diameter for a given segment of lumen, the stent could advantageously provide appropriate outward forces and resistance to collapse for a lumen of that size.

Clinical Requirements

Constant Forces While Constrained in "Undersized" Vessels

Because it is common practice to "oversize" a self-expanding stent for the lumen to be treated (e.g., placing an 8 mm stent in a 7 mm artery), a self-expanding stent should generate the desired outward pressure when the stent is compressed by an appropriate amount, typically 1 mm to 2 mm for typical arteries.

Graduated Forces Along Stent Axis

In other clinical situations, it may be desirable to implant a self-expanding stent that produces greater pressure against the lumen wall at either the small or large end, according to the decision of the physician in treating a particular diseased artery. Thus, it may be advantageous to provide a tapered stent that exerts different pressure along its length, not necessarily in proportion to its local diameter. In fact, it may be advantageous to treat a tapered segment of artery with a stent that expands freely to a constant diameter along its length (i.e., a non-tapered stent) but exerts graduated pressure along its length. Such a stent would not appear tapered in a freely expanded condition but, because it would exert a graduated amount of pressure along its length, it may still be considered a tapered stent. For these reasons, a tapered stent should achieve the desired graduated pressure along its length, though it may or may not assume a tapered shape when fully and freely expanded.

Retention Requirements for Self-Expanding Stents

In some cases, physicians prefer self-expanding stents to have specific features on the distal end to aid in securing the stent to the lumen wall as it is expanded into place. Such features usually include arms, petals, or a circumferential ring of stent material that engages the lumen wall as the stent is allowed to expand into place.

Typically, self-expanding stents are introduced through the body lumen to the position where the physician wishes to allow the stent to expand to treat a local disease condition. Expansion is carried out by most stent deployment systems progressively from the distal end toward the proximal end by a retractable sheath covering the stent and retaining the stent in its compressed state. Under physician control, the covering sheath is withdrawn proximally, exposing the distal end of the stent. As the compressed stent is exposed, it expands. Stents are chosen to be of a size that, when fully expanded, assumes a diameter larger than the lumen to be treated; so, as the stent expands, it will contact the lumen wall, creating a frictional engagement and preventing any relative movement of the stent and lumen wall. This positive initial engagement helps to assure that the deployed stent will remain in the position intended by the physician.

To enhance this frictional engagement, it is common in the art to form stents such that the most distal end of the stent expands to a larger diameter than the middle portion of the stent (when freely expanded). For symmetry, and perhaps to assure frictional engagement at the proximal end of the stent as well, it is common for such stents to have both distal and proximal ends so formed. Thus, it is advantageous to provide a stent with an end or ends that enhance the frictional engagement of the stent with the lumen wall during deployment.

In non-helical designs, typically constructed with circumferential rings joined axially to form a tubular structure, the most distal and proximal ends are formed (in the fully-expanded state) into a conical shape with the largest diameter at end of the stent. Alternately, additional features may be added to the distal and proximal ends of tubular structure to form this outward-expanding conical shape. Such features take the form of petals, struts, closed cells, tabs containing radiopaque markers, and so forth.

End Treatments for Helical Stents

Helical stent configurations are different from non-helical (hoop-plus-bridge) configurations because the ends of a helix do not form an end that closely approximates the end of a right cylinder (i.e., the end of a helix is not perpendicular to its longitudinal axis). For example, Corso, (U.S. Pat. No. 5,913,897) discloses a helical stent configuration with uneven ends.

It is known in the art to apply end treatments to helical stents to make them approximate a right cylinder (or a right conical cylinder, if the end is flared). One such treatment (e.g., Cottone) adds a transition segment and a cylindrical hoop to the ends of the stent as shown in FIG. 14. Another method of making even the end of a helical stent is taught by Hojeibane (U.S. Pat. No. 6,423,091) and includes progressively lengthening the struts of the final turn of the helix as shown in FIG. 15. A third method of providing a perpendicular end to a helical stent is disclosed by the inventor of the present application in U.S. Patent Publication Nos. 2006/0060266, 2006/0064154, 2006/0064155, 2006/0064158, and 2006/0074480. In that method, a series of paddles is added to the end of the stent; the length of the paddles is varied so that, even though the helical array of stent struts ends in a helical plane, the ends of the paddles are evenly aligned to create a right cylindrical end to the stent as shown in FIG. 16.

All of these methods create a more even end for a helical stent so that the ends of the stent engage the lumen wall in an axially symmetrical way, without creating any local irregularities where the helix ends. Also, by providing a substantially perpendicular surface at the proximal end of the stent, the engaging portions of the delivery system that exert axial pushing forces on the proximal end of the stent during deployment are simplified, and the pushing forces are more uniformly distributed onto the stent, preventing buckling or distortion of the stent during deployment. For these reasons it is advantageous to provide a helical stent with one or both ends treated to approximate the end of a right circular cylinder.

If the prior art stents are expanded into a non-cylindrical shape (e.g., with a non-cylindrical balloon), then the openings (referred to as pores herein) become asymmetrical. More specifically, if a cylindrical stent having same size pores is deformed to have one end be larger than the opposite end, the pores at the smaller end will be smaller than the pores at the larger end. The opening size of the pores defines the lower limit of objects that can pass therethrough, e.g., emboli. If the pore openings are constant, such as in the case of a prior art cylindrical stent, then an upper emboli limit can be defined and practiced. However, when such a cylindrical stent is deformed to a taper, for example, the pores at the larger end are greater in size than the pores at the smaller end. Such a configuration can impermissibly permit passing of emboli greater than the desired upper limit. It would, therefore, be beneficial to provide a tapered stent having pores that are substantially uniform along the length of the stent. As used herein, pores, pore size, and/or pore openings refer to the openings that exist in an expanded form of the stent and have four sides, two of which are defined by a first set of struts and at least one loop and a second set of struts and at least one loop on an adjacent turn of the helical winding. The other two sides are defined by two adjacent bridges connecting the turn on which the first set of struts exist to the adjacent turn on which the second set of struts exist. Therefore, the size of the pore is the area defined by these four sides when the stent is expanded and also defines the upper emboli limit. The pore size can also be defined by the size of the particle that can pass therethrough or the area of the pore. Because helical stents are typically cut from metal tubes, the pore boundary can also be defined by a proportion of metal area to the total area within a region, which proportion can be explained as a percentage of metal within a given area of the stent.

It would be desirable, however, to provide a practical non-cylindrical helical stent (i.e., tapered or flared shape), whether self-expanding or balloon-expandable, having a varying gradient of properties over the length thereof achieving a maximum recovery performance and substantially no change in axial length upon expansion. It would also be beneficial to provide measures for smoothly changing the properties of a stent manufactured from a tube from one end to the other.

SUMMARY OF THE INVENTION

It is accordingly an object of the present invention to provide a tapered helical stent and a method for manufacturing the stent that overcome the hereinafore-mentioned disadvantages of the heretofore-known devices and methods of this general type and that provides a practical non-cylindrical helical stent having a perpendicular end and a smoothly varying gradient of properties over the length thereof achieving a maximum recovery performance and substantially no change in axial length upon expansion, and that provides measures for smoothly changing the properties of a stent manufactured from a tube from one end to the other.

The tapered helical stent of the present invention provides pores that are substantially uniform along the length of the stent. Therefore, the tapered helical stent has the ability to define an upper emboli limit, which limit can be explained by the area of the cell, the boundary of the cell, the upper limit on size of a particle that can pass therethrough, and/or the percentage of metal in a given area of the stent. Accordingly, the tapered helical stent of the present invention can be formed to have a substantially constant pore area, a substantially constant pore boundary, a defined upper particle size limit, and a constant proportion of metal area to total area within a given region.

Constant Pressure at Each Point Along the Stent

In the case of self-expanding stents, the stent should generate expansion forces (Chronic Outward Force, also referred to as COF) and resistance to forces (Radial Resistive Force, also referred to as RRF) appropriate for the lumen diameter at each segment along its length.

While there is a paucity of clinical evidence relating outward forces or pressure against the vessel wall with clinical effects for different sizes and types of vessels, it is thought that smaller vessels should require smaller expansion forces than larger vessels. The invention of the instant application proposes that the pressure against the vessel wall, in units of force per unit area, should be approximately the same for large and small vessels. Therefore, a tapered stent should apply an equal amount of pressure to the lumen wall at every point along its length.

Balloon-expanded stents are not generally configured to provide constant pressure against the vessel wall. However, the expansion of the stent is achieved by pressurizing a balloon, so it is advantageous if the resistance to expansion of the stent at each point along its length is proportional to the intended vessel size; thus, a balloon expanded by hydrostatic pressure (equal at all points on the balloon surface) will cause the stent to expand to the desired diameter at each point along its length. For example, a stent configured according to such criterion and intended for a vessel that tapers from 8 mm diameter to 6 mm diameter should expand to these diameters when forced outward by a balloon inflated to the appropriate pressure. Thus, according to the present invention, similar design considerations are used to construct tapered stents whether they are self-expanding or balloon-expanded.

By providing a tapered helical stent that can linearly increase features, the pores can be shaped to define openings both at the smaller end and the larger end having virtually the same shape and area.

With the foregoing and other objects in view, there is provided, in accordance with the invention, a tapered helical implantation device for peripheral arteries and other body lumina of locally varying diameter, including struts connected by loops and shaped in a helical winding, the helical winding defining turns and, when expanded, having a first end with a first expanded circumference, and a second end with a second expanded circumference greater than the first expanded circumference to form a stent tapering outward from the first end towards the second end, bridges connecting adjacent ones of the turns, and the struts, the loops, and the bridges defining a series of pores aligned along the helix, the pores having a substantially uniform pore size.

With the objects of the invention in view, there is also provided a tapered helical implantation device for peripheral arteries and other body lumina of locally varying diameter, including a helical winding of struts connected by loops, the helical winding defining a first end, a second end, and helical turns, the struts each having a length and a width, at least one of the length of the struts, the width of the struts, and a frequency of the struts per one of the turns being varied from the first end to the second end to form a diameter-varying implantable stent outwardly tapered from the first end to the second end when expanded, bridges connecting adjacent ones of the turns, and the struts, the loops, and the bridges defining a series of pores aligned along the helix, the pores having a substantially uniform pore size.

With the objects of the invention in view, there is also provided an implantation device for lumina of locally varying diameter, including a helical winding defining turns and, when expanded, having a first end with a first expanded circumference and a second end with a second expanded circumference greater than the first expanded circumference to form a stent tapering outward from the first end towards the second end, bridges connecting adjacent ones of the turns, and the winding and the bridges defining a series of pores aligned along the helix, the pores having a substantially uniform pore size.

With the objects of the invention in view, there is also provided a tapered helical implantation device for peripheral arteries and other body lumina of locally varying diameter, including struts connected by loops and shaped in a helical winding, the helical winding defining turns and, when expanded, having a first end with a first expanded circumference, and a second end with a second expanded circumference greater than the first expanded circumference to form a stent tapering outward from the first end towards the second end, bridges connecting adjacent ones of the turns, and the struts, the loops, and the bridges defining a series of pores aligned along the helix, the pores being shaped to permit particles no greater than a given size to pass therethrough, the given size being substantially constant from the first end to the second end.

With the objects of the invention in view, there is also provided a tapered helical implantation device for peripheral arteries and other body lumina of locally varying diameter, including a helical winding of struts connected by loops, the helical winding defining a first end, a second end, and helical turns, the struts each having a length and a width, at least one of the length of the struts, the width of the struts, and a frequency of the struts per one of the turns being varied from the first end to the second end to form a diameter-varying implantable stent outwardly tapered from the first end to the second end when expanded, bridges connecting adjacent ones of the turns, and the struts, the loops, and the bridges defining a series of pores aligned along the helix, the pores being shaped to permit particles no greater than a given size to pass therethrough, the given size being substantially constant from the first end to the second end.

With the objects of the invention in view, there is also provided a tapered helical implantation device for peripheral arteries and other body lumina of locally varying diameter, including metal struts connected by metal loops and shaped in a helical winding, the helical winding defining turns and, when expanded, having a first end with a first expanded circumference, and a second end with a second expanded circumference greater than the first expanded circumference to form a stent tapering outward from the first end towards the second end, the first end having a first end turn and the second end having a second end turn, metal bridges connecting adjacent ones of the turns, and the struts, the loops, and the bridges between the first and second end turns having a substantially constant metal-to-total area proportion.

With the objects of the invention in view, there is also provided a tapered helical implantation device for peripheral arteries and other body lumina of locally varying diameter, including a helical winding of struts connected by loops, the helical winding defining a first end, a second end, and helical turns, the first end having a first end turn and the second end having a second end turn, the struts each having a length and a width, at least one of the length of the struts, the width of the struts, and a frequency of the struts per one of the turns being varied from the first end to the second end to form a diameter-varying implantable stent outwardly tapered from the first end to the second end when expanded, bridges connecting adjacent ones of the turns, and the struts, the loops, and the bridges between the first and second end turns having a substantially constant metal-to-total area proportion.

With the objects of the invention in view, there is also provided a implantation device for lumina of locally varying diameter, including a helical winding of struts connected by loops and defining a first end, a second end, and helical turns, bridges connecting adjacent ones of the turns, and the struts each having a length and a width, at least one of the length of the struts, the width of the struts, and a frequency of the struts per turn being varied from the first end to the second end to form a diameter-varying implantable stent outwardly tapered from the first end to the second end when expanded.

With the objects of the invention in view, there is also provided a implantation device for lumina of locally varying diameter, including a helical winding of struts connected by loops and defining a first end, a second end, and helical turns, bridges connecting adjacent ones of the turns, and the struts each having a length and a width, at least two of the length of the struts, the width of the struts, and a frequency of the struts per turn being varied from the first end to the second end to form a diameter-varying implantable stent outwardly tapered from the first end to the second end when expanded.

With the objects of the invention in view, there is also provided a implantation device for lumina of locally varying diameter, including a helical winding of struts connected by loops and defining a first end, a second end, and helical turns, bridges connecting adjacent ones of the turns, and the struts each having a length varied from the first end to the second end to form a diameter-varying implantable stent outwardly tapered from the first end to the second end when expanded.

With the objects of the invention in view, there is also provided a implantation device for lumina of locally varying diameter, including a helical winding of struts connected by loops and defining a first end, a second end, and helical turns, bridges connecting adjacent ones of the turns, and the struts each having a width varied from the first end to the second end to form a diameter-varying implantable stent outwardly tapered from the first end to the second end when expanded.

With the objects of the invention in view, there is also provided a implantation device for lumina of locally varying diameter, including a helical winding of struts connected by loops and defining a first end, a second end, and helical turns, bridges connecting adjacent ones of the turns, and the struts having a frequency per turn varied from the first end to the second end to form a diameter-varying implantable stent outwardly tapered from the first end to the second end when expanded.

In accordance with another feature of the invention, the winding defines a longitudinal axis of the stent and an axis of the helical winding; and the struts extend one of longitudinally along the longitudinal axis and perpendicular to the axis of the helical winding.

In accordance with a further feature of the invention, the bridges connect adjacent loops on adjacent ones of the turns.

In accordance with an added feature of the invention, the bridges are placed at locations on the helix corresponding to at least one of every third strut pair, every fifth strut pair, and every seventh strut pair.

In accordance with an additional feature of the invention, the bridges are disposed in a 5-up-and-5-down pattern or a 5-up-and-7-down pattern.

In accordance with yet another feature of the invention, the stent has an overall length and a number of the struts per one of the turns remains the same throughout the overall length.

In accordance with yet a further feature of the invention, the struts increase in one of width and length from the first end to the second end at least one of in steps, by linear proportion, and by geometric proportion.

In accordance with yet an added feature of the invention, the struts of each of the turns have the same size and the struts increase in size from one of the turns to another of the turns from the first end to the second end at least one of in steps, by linear proportion, and by geometric proportion.

In accordance with yet an additional feature of the invention, a density of the bridges is substantially even over the overall length to have an equal number of the struts disposed between adjacent bridges in all areas of the stent.

In accordance with again another feature of the invention, a number of the struts per one of the turns is constant and a pattern of the bridges remains constant along the overall length.

In accordance with again a further feature of the invention, a density of the bridges is varied over the overall length to have a different number of the struts disposed between adjacent ones of the bridges in different areas of the stent.

In accordance with again an added feature of the invention, a circumferential distance between ends of the struts at the second end are substantially the same as a circumferential distance between ends of the struts at the first end to create the substantially uniform pore size.

In accordance with again an additional feature of the invention, a number of the struts at the second end is proportionally larger than a number of the struts at the first end.

In accordance with still another feature of the invention, the first end has a diameter between approximately 4 mm and approximately 6 mm and the second end has a diameter between approximately 6 mm and approximately 10 mm.

In accordance with still a further feature of the invention, the stent has a length and, when expanded and placed in a lumen, provides a constant hoop force over the length against the lumen.

In accordance with still an added feature of the invention, the stent has a constant metal ratio from the first end to the second end.

In accordance with still an additional feature of the invention, the lumen is one of a carotid artery, a common bile duct, and a location where an iliac artery joins a superficial femoral artery.

In accordance with another feature of the invention, the stent is a balloon-expanded stent and has a resistance to expansion at each point along a length of the stent proportional to an intended vessel size in which the stent is to be implanted.

In accordance with a further feature of the invention, the struts and the loops define a kerf having a width, the width of the kerf between the struts defines the width of the struts, and the kerf is varied along the stent to create a taper of the stent when expanded.

In accordance with an added feature of the invention, a width of the struts remains constant throughout the overall length, a width of the kerf between the struts remains constant throughout the overall length, a number of struts per one of the turns stays the same along an entirety of the overall length, and the length of the struts varies from the smaller end to the larger end.

In accordance with an additional feature of the invention, both the width and the length of the struts transition in a constantly increasing manner from the smaller end of the stent to the larger end, the kerf transitions in a constantly decreasing manner from the smaller end to the larger end, and a number of the struts per one of the turns remains the same along an entirety of the overall length.

In accordance with yet another feature of the invention, both the width and the length of the struts transition in a constantly increasing manner from the smaller end to the larger end, the kerf remains constant throughout the overall length, and a number of the struts per one of the turns decreases along the overall length from the smaller end to the larger end.

In accordance with yet a further feature of the invention, the length and the width of the struts and a count of the struts varies along the overall length to have a number of the struts at the smaller end be larger than a number of the struts at the larger end.

In accordance with yet an added feature of the invention, the stent is a tapered balloon-expanded stent and has a resistance to expansion at each point along the overall length proportional to an intended implantation vessel size.

In accordance with yet an additional feature of the invention, the struts and the loops are shaped to expand asymmetrically when the stent is expanded by a uniform expansion force.

In accordance with again another feature of the invention, the stent has a uniform resistance to expansion and has uniform expansion properties over the overall length when expanded to an asymmetric shape.

In accordance with again a further feature of the invention, the stent is a self-expanding tapered helical stent and generates expansion forces and resistance to external forces proportional to an adjacent lumen diameter at each point along the overall length to apply a substantially equal pressure to an implantation lumen wall at every point along the overall length.

In accordance with a concomitant feature of the invention, an opening angle between struts of a pair of the struts is uniform over the overall length.

Other features that are considered as characteristic for the invention are set forth in the appended claims.

Although the invention is illustrated and described herein as embodied in a tapered helical stent and method for making the stent it is, nevertheless, not intended to be limited to the details shown and described because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

BRIEF DESCRIPTION OF THE DRAWINGS

FIG. 7 is a fragmentary, side elevational view of a portion of a seventh prior art stent configuration;

FIG. 8 is a fragmentary, side elevational view of an eighth prior art stent configuration;

FIG. 9 is a fragmentary plan view of the stent configuration of FIG. 8;

FIG. 10 is a perspective view of a ninth prior art stent configuration;

FIG. 11 is a fragmentary plan view of a portion of a tenth prior art stent configuration;

FIG. 12 is a fragmentary plan view of a portion of an eleventh prior art stent configuration;

DETAILED DESCRIPTION OF THE PREFERRED EMBODIMENTS

Figure 1:
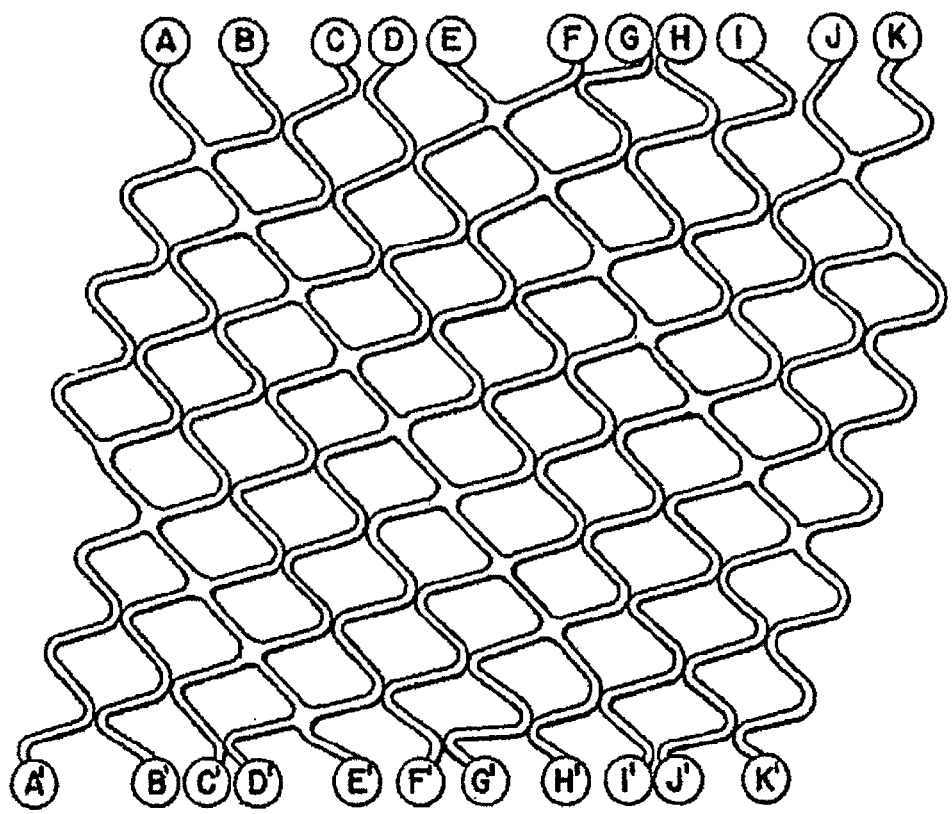
FIG. 1 is a fragmentary plan view of a portion of a first prior art stent configuration.

While the specification concludes with claims defining the features of the invention that are regarded as novel, it is believed that the invention will be better understood from a consideration of the following description in conjunction with the drawing figures, in which like reference numerals are carried forward.

Before the present invention is disclosed and described, it is to be understood that the terminology used herein is for the purpose of describing particular embodiments only and is not intended to be limiting. It must be noted that, as used in the specification and the appended claims, the singular forms "a," "an," and "the" include plural references unless the context clearly dictates otherwise.

The present invention presents, for the first time, a tapered stent having a helical configuration, referred to herein as a tapered helical stent. Construction of a tapered helical stent can be explained with reference to FIGS. 17, 18, and 19. In general, helical stents include a continuous helical structure (typically made of a string of cells or an undulating pattern of struts and end-loops) with joining structures (bridges) connecting adjacent turns of the helix to provide mechanical integrity to the tubular structure and prevent unwinding, kinking, and buckling. If the bridge pattern is constant, prior art cylindrical helical stents will define pores with a constant size—thereby defining an upper size limit for a spherical particle that can pass through the stent wall. This pore consistency is not present if such a stent is, hypothetically, deformed to taper. The tapered helical stent of the present invention, however, varies features of the stent to keep constant the pore size and, therefore, keep constant the upper spherical size limit for particles that can pass therethrough.

Figure 2:
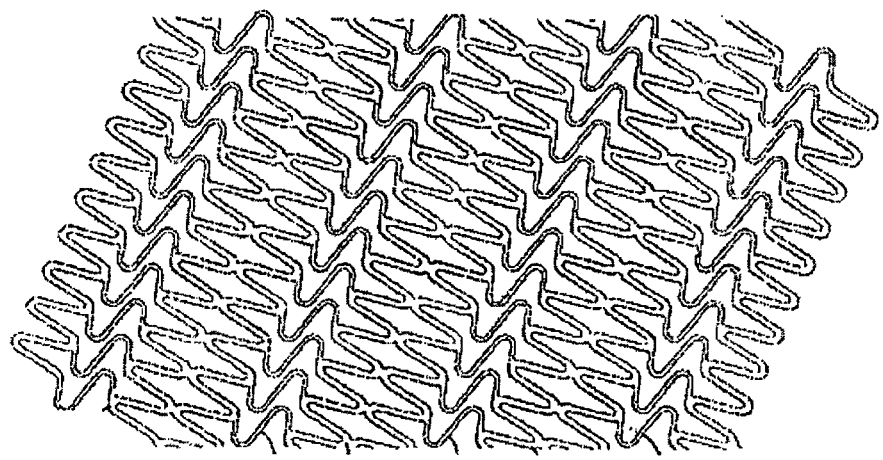
FIG. 2 is a fragmentary plan view of a portion of a second prior art stent configuration.
Figure 3:
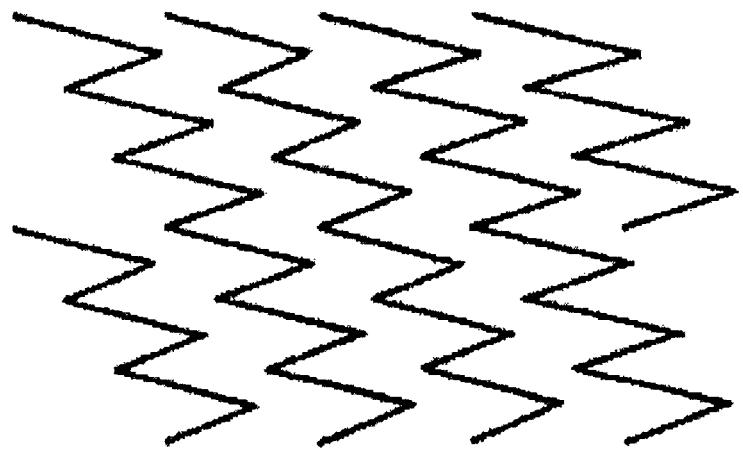
FIG. 3 is a fragmentary plan view of a portion of a third prior art stent configuration.
Figure 4:
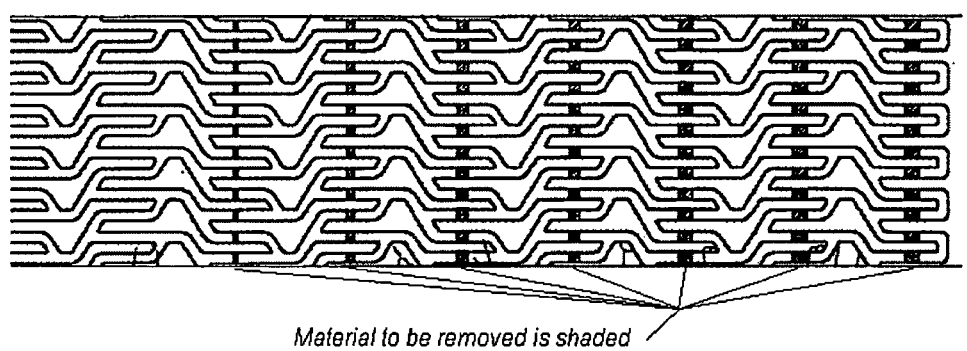
FIG. 4 is a fragmentary plan view of a portion of a fourth prior art stent configuration.
Figure 5:
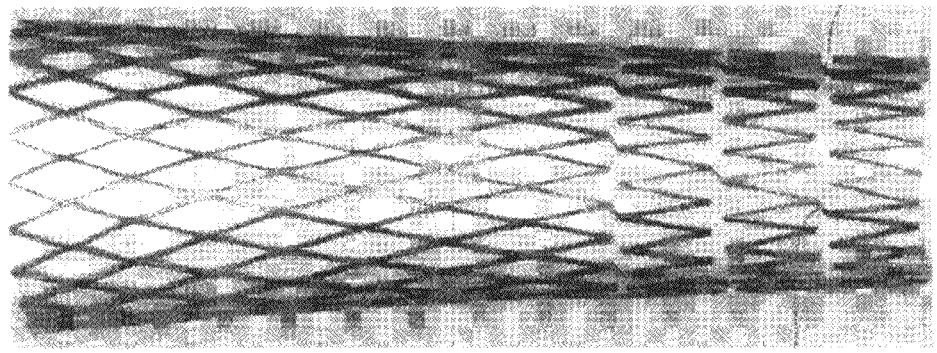
FIG. 5 is a fragmentary, side elevational view of a portion of a fifth prior art stent configuration.
Figure 6:
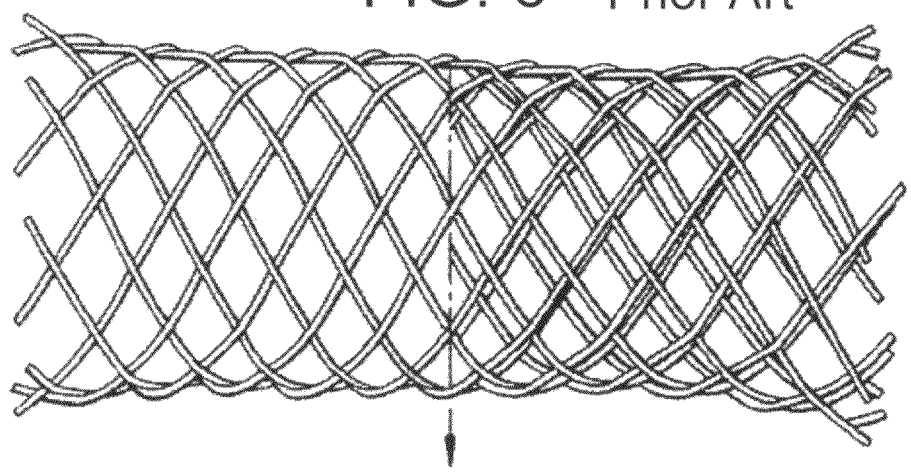
FIG. 6 is a fragmentary, side elevational view of a portion of a sixth prior art stent configuration.
Figure 13:
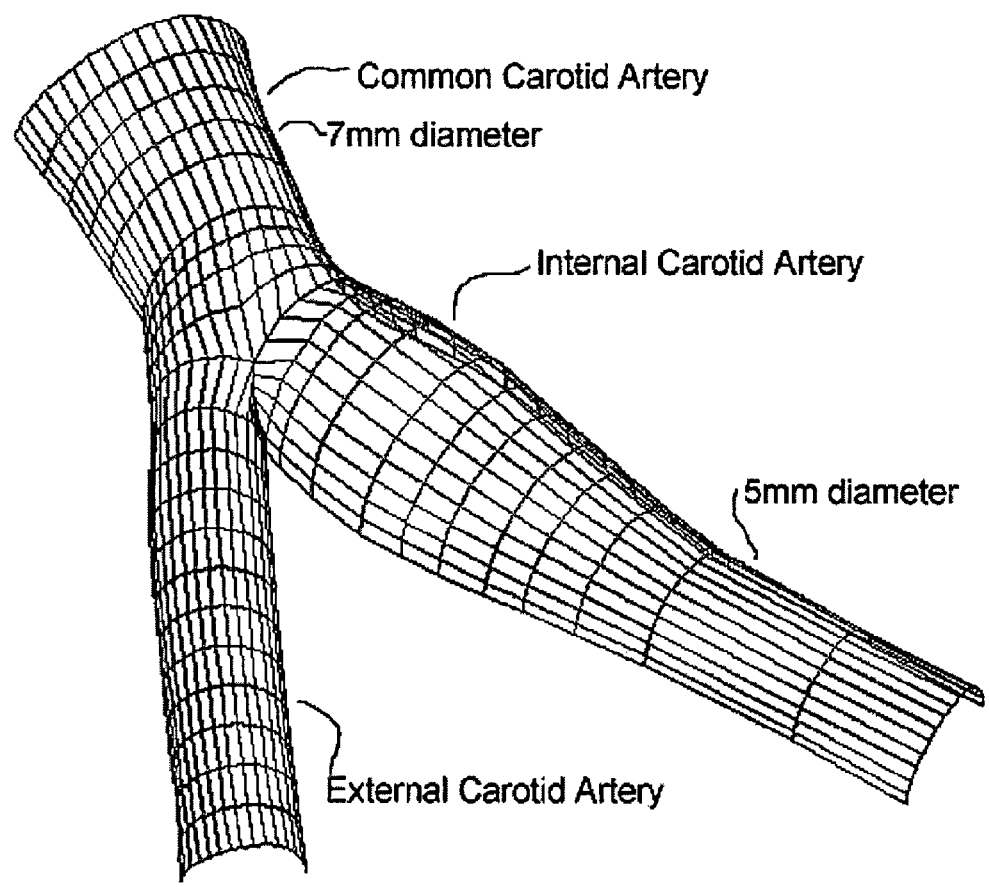
FIG. 13 is a fragmentary perspective view of the common, internal, and external carotid arterial junction.
Figure 14:
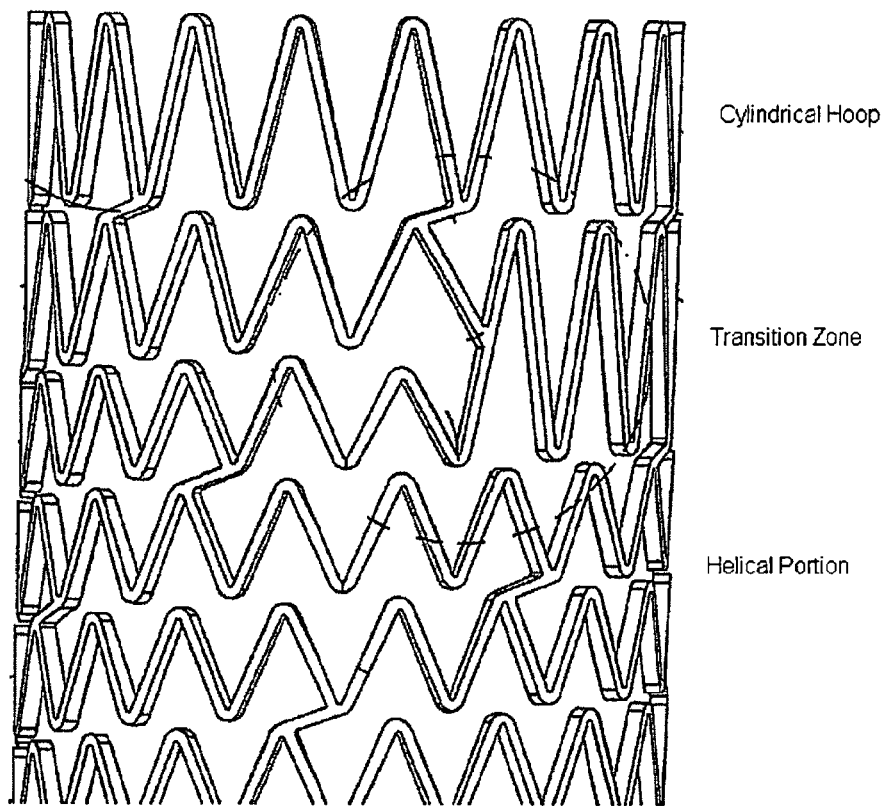
FIG. 14 is a fragmentary, side elevational view of a twelfth prior art stent configuration.
Figure 15:
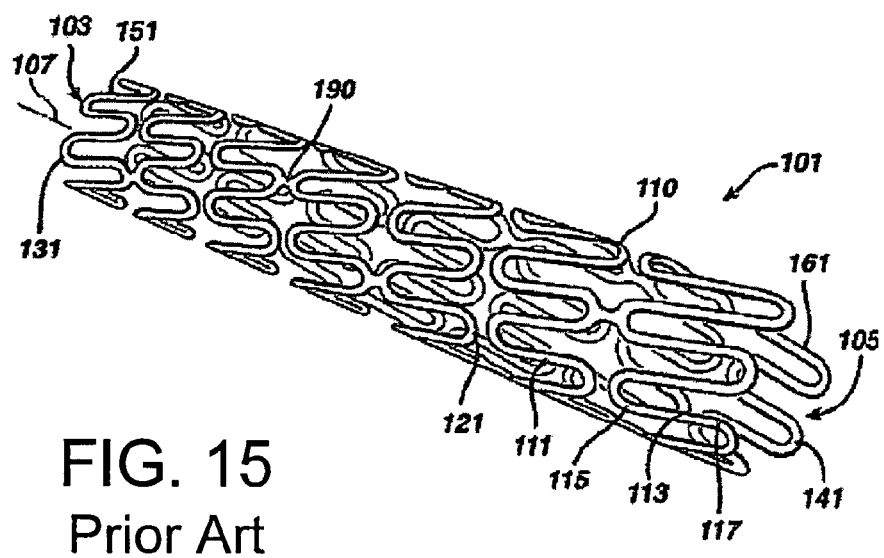
FIG. 15 is a perspective view of a thirteenth prior art stent configuration.
Figure 16:
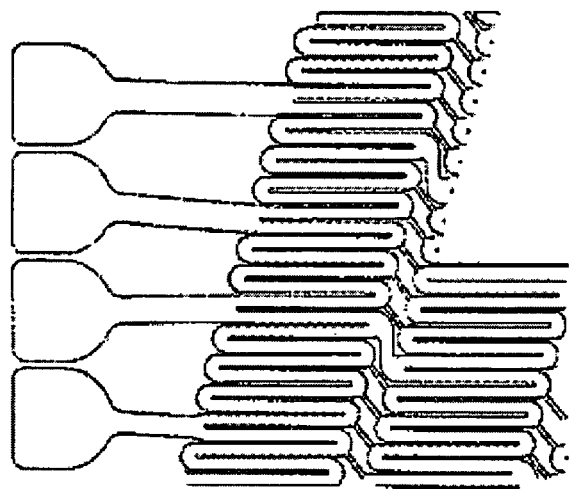
FIG. 16 is a fragmentary, plan view of a portion of a fourteenth prior art stent configuration.
Figure 17:
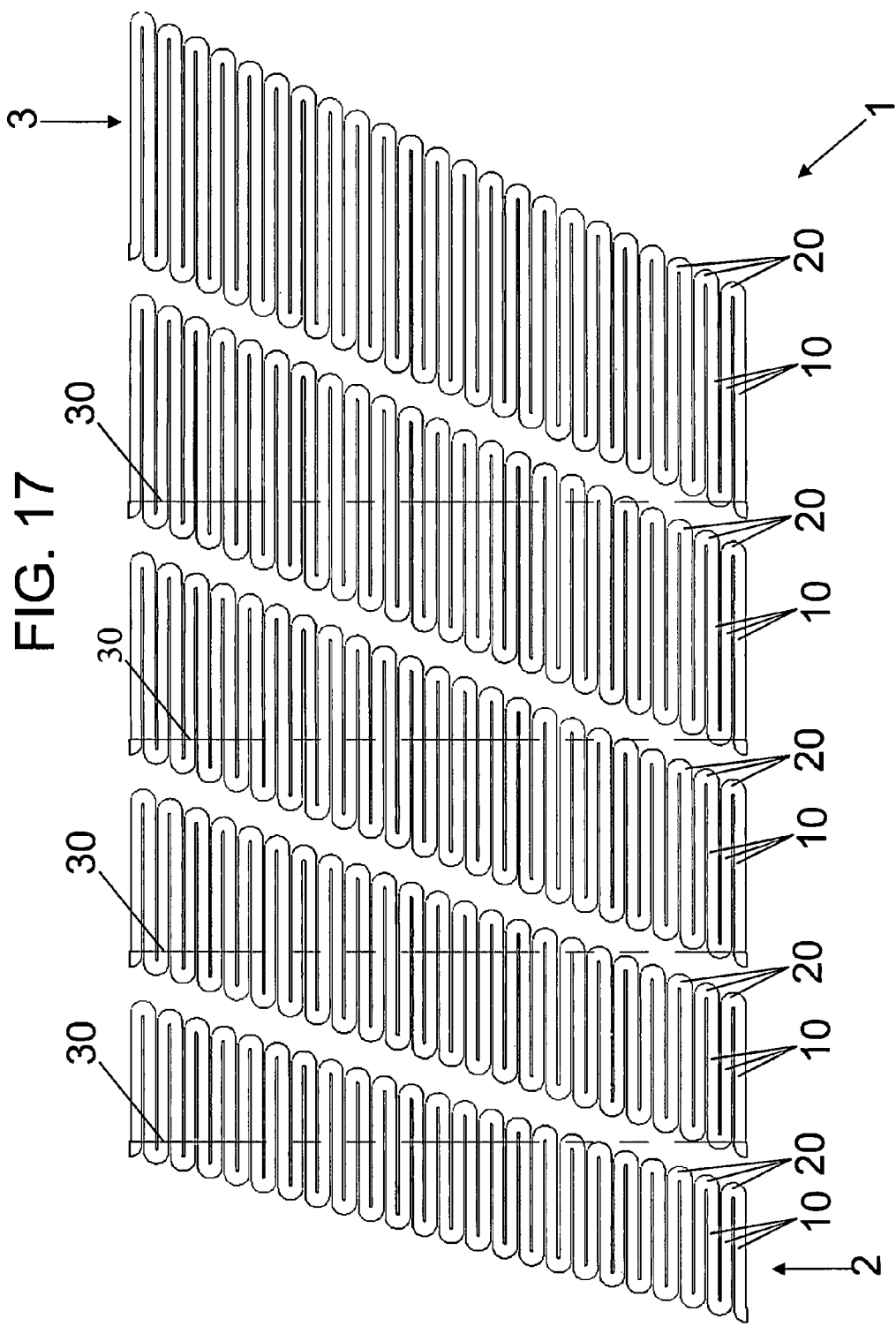
FIG. 17 is a fragmentary, enlarged, planar projection of a portion of an exemplary configuration of a tapered helical stent according to the invention.
Figure 18:
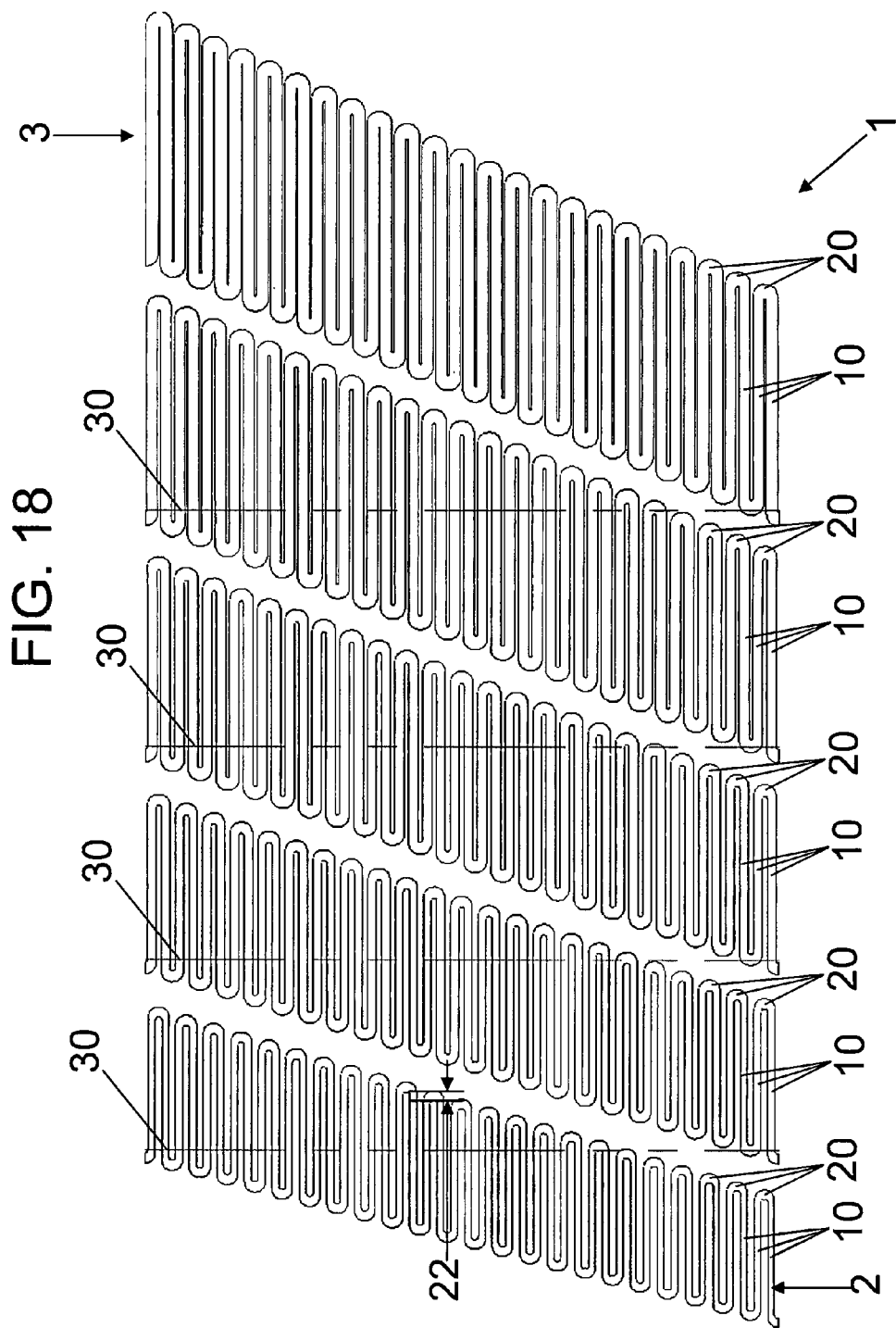
FIG. 18 is a fragmentary, enlarged, planar projection of a portion of another exemplary configuration of a tapered helical stent according to the invention.
Figure 19:
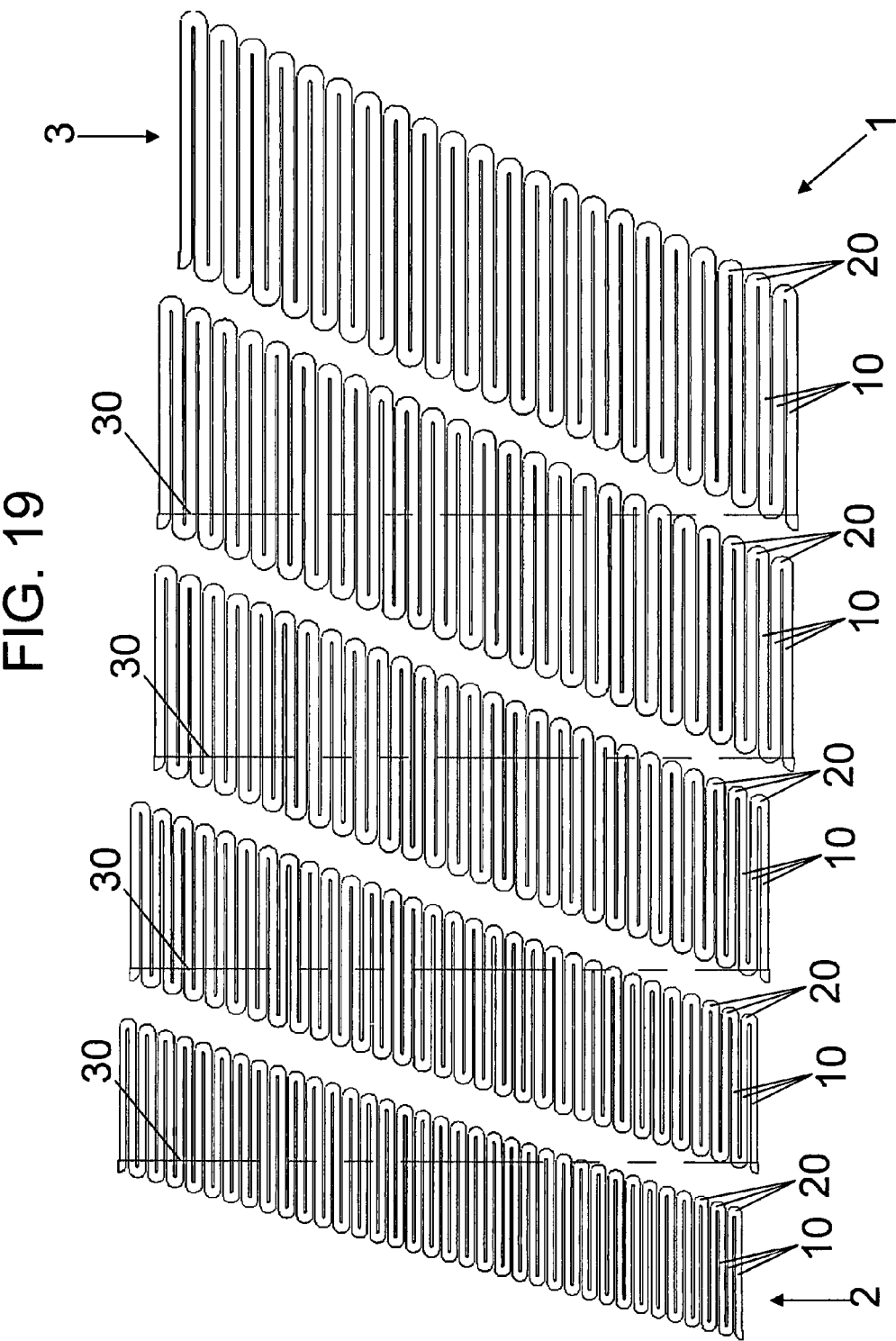
FIG. 19 is a fragmentary, enlarged, planar projection of a portion of a further exemplary configuration of a tapered helical stent according to the invention.

FIGS. 17 to 19 show three different embodiments of the tapered helical stent of the present invention (bridges are omitted for clarity). Each of the configurations show the helical structure having struts 10 connected by loops 20. FIGS. 17 to 19 are planar representations of the helical structure, much like a Mercator projection of the spherical Earth. Here, the approximately tubular form is cut longitudinally and flattened. To illustrate the single helical winding connection of the structures of FIGS. 17 to 19, dashed vertical lines 30 are included (four lines in each of the figures). These lines 30 indicate the junction of two halves of a single loop 20. In these figures, the struts 10 are aligned along the axis of the stent 1, but they also can be aligned perpendicular to the axis of the helical winding (as in the configuration of FIG. 2). Each of the five planar segments shown in FIGS. 17 and 19 will be referred to as a "turn" of the helical winding. Between adjacent turns of this winding are the non-illustrated bridges, which join a loop of one turn to another nearby loop of an adjacent turn and which are described in further detail below and shown in FIG. 20.

There are three characteristics of the helical winding that permit the construction of the tapered helical stent 1 of the present invention: strut width, strut length, and kerf (which is the size and shape of the cut that creates the struts 10 and loops 20. As set forth above, helical stents are typically cut from a solid tube of material (e.g., with a laser). The width of the kerf between the struts is used by the present invention to define the width of the struts 10 and the size of this kerf can be varied along a stent to create the taper of the instant invention. Heretofore, construction of a stent having varying strut width or strut length or kerf was not possible. With the ability of the present invention to vary these three characteristics, the tapered helical stent becomes possible.

A first exemplary stent configuration according to the invention is illustrated in FIG. 17. Here, the width of the struts 10 remains constant throughout the length of the stent 1. Also, the width of the kerf between the struts 10 remains constant throughout the length of the stent 1. This means that the number of struts 10 per turn stays the same along the entire length of the stent 1. It is the strut length that varies from the smaller end 2 of the stent 1 to the larger end 3 in this embodiment.

A second exemplary stent configuration according to the invention is illustrated in FIG. 18. Here, both the width and the length of the struts 10 transition in a constantly increasing manner from the smaller end 2 of the stent 1 to the larger end 3 of the stent 1. The kerf, in comparison, transitions in a constantly decreasing manner from the smaller end 2 of the stent 1 to the larger end 3 of the stent 1. Like the first configuration, the number of struts 10 per turn remains the same along the entire length of the stent 1.

One illustrative exemplary configuration for this tapered helical stent has a single turn length of 5.6549 mm—the turn length is equal to the length of the vertical lines 30. This stent is selected to have a starting strut length of 1 mm and a starting strut width of 0.054 mm. For a stent having a total longitudinal length of 40 mm, the ending strut length is 1.929 mm and the ending strut width is 0.11 mm.

A third exemplary stent configuration according to the invention is illustrated in FIG. 19. Here, both the width and the length of the struts 10 transition in a constantly increasing manner from the smaller end 2 of the stent 1 to the larger end 3 of the stent 1. In contrast to FIG. 18, here the kerf remains constant throughout the length of the stent 1. Therefore, the number of struts 10 per turn decreases along the length of the stent 1 from the smaller end 2 of the stent 1 to the larger end 3 of the stent 1.

By varying or keeping constant any of the strut length, the strut width, and the kerf, the helical stent can be configured to have any desired kind of taper. Variables for creating a final tapered helical stent include:
- apex offset (longitudinal distance from the end of the kerf at an apex to the end of the apex; see reference numeral 22 in FIG. 18);
- desired first strut length;
- desired last strut length;
- outer tube diameter (O/D);
- start angle (of strut offset);
- strut length growth percentage; and
- either:
  - strut length-to-width ratio; or
  - desired first and last strut widths.

With defined values for each of these variables, a customized (or standardized) tapered helical stent can be created.

Figure 20:
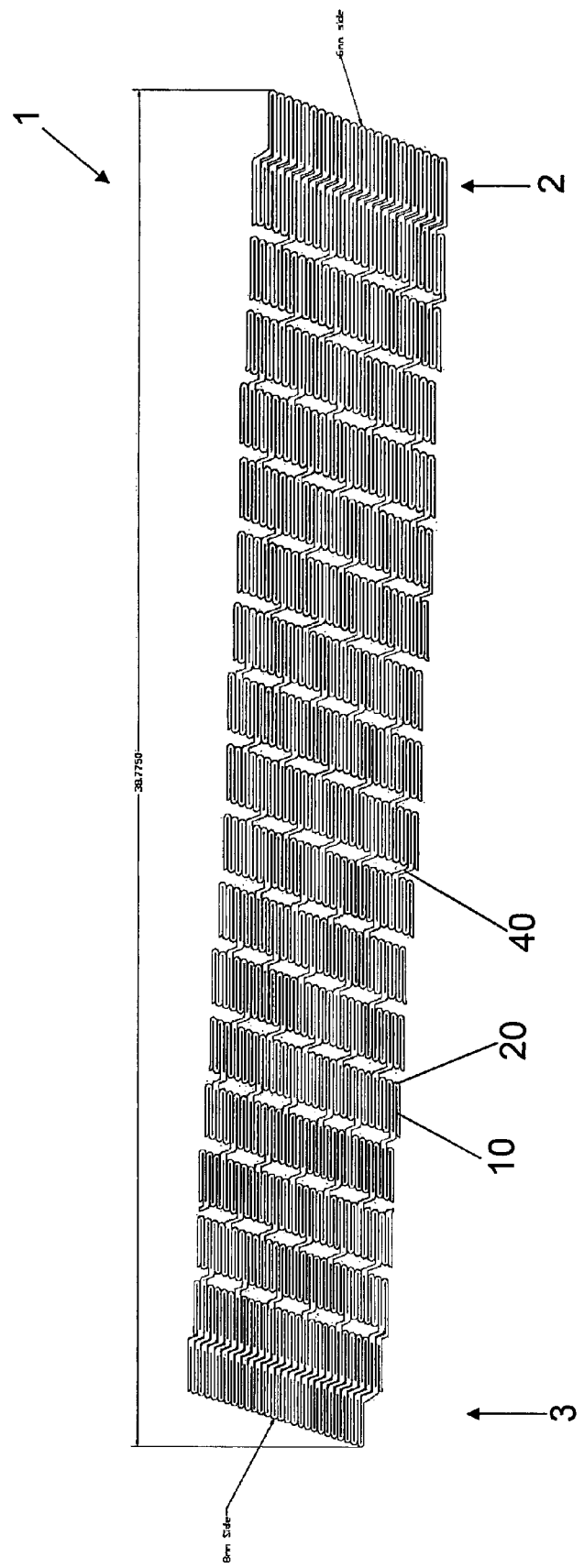
FIG. 20 is a fragmentary, enlarged, planar projection of a portion of still another exemplary configuration of a tapered helical stent according to the invention.

FIG. 20 is an exemplary configuration for a tapered helical stent 1 of the present invention. This exemplary stent 1 varies the strut length, the strut width, and the strut count so that the number of struts 10 at the smaller end 2 is slightly larger (twenty-two pairs) than the number of struts 10 at the larger end 3 (thirty-two and ½ pairs). Bridges 40 are illustrated in FIG. 20 and connect a loop 20 on one side of a turn to a loop 20 on an opposing side of an adjacent turn. Here, the bridges 40 are in a 5-up-and-5-down pattern. It can be seen in FIG. 20 that bridges 40 connect each of the first turn struts 10 to one strut 10 in the second turn. This configuration provides a good balance of flexural stiffness and integrity in the main body of the stent with an increased resistance to buckling at each end, providing greater ability to accommodate the forces applied to deploy the stent; this design also provides a gradual transition from a smaller diameter of 6 mm to a larger diameter of 8 mm after expansion. By providing a larger number of struts (and, hence, opening angles) at the small end of the stent, the outward forces at that end would be lower than those at the larger end of the stent.

In an exemplary embodiment where the number of struts per turn stays the same (see FIGS. 17 and 18), a tapered helical stent can be created with a larger end 3 opening of 8 mm and a smaller end opening of 6 mm. For example, a 5-up-and-7-down configuration can be used to create a uniform pattern of bridges in a 46 strut-per-turn design as shown in FIGS. 17 and 18. The number of struts 10 for the 8 mm opening is selected. Then, a strut length and a strut width are determined for a 6 mm opposite end having the same number of struts 10. The selection criteria for this embodiment include keeping the same opening angle in the expanded condition. This means that the 6 mm end has struts 75% as long as the 8 mm end. Because the strut width is proportional to the strut length, the 6 mm end has struts 75% as wide as the 8 mm end.

In one variation of struts 10 in such a stent, the struts 10 change smoothly from the 8 mm end to the 6 mm end, each one being different in length and width. Such a configuration is illustrated in FIGS. 17 and 18, for example. Alternatively, in a non-illustrated configuration, the struts 10 can change in jumps, with all of the struts in one turn, for example, being the same length and width. Accordingly, for a fifty-turn 50 mm stent, fifty different strut geometries can exist, for example. In another exemplary configuration, three segments can be created for the stent (one for 6 mm, one for 7 mm, and one for 8 mm) with the strut characteristics changing from one step to the other.

As set forth above, a further exemplary tapered helical stent according to the present invention can be configured to have a smooth or gradual incremental progression of either the number of struts per unit length or the strut size from one end of the stent to the other, or even both the number of struts and the strut size. Such a gradual change in struts per turn and/or strut size cannot be achieved in a stent configured according to the prior art, either by the known cylindrical-hoop structures or the uniform helical structures. When the number of struts per unit length and their dimensions are varied in a progressive manner, when the stent is expanded, the properties at each point along the length of the stent are appropriate for a stent (and, hence, the stented lumen) of that size.

Alternately, the struts may be varied in groups; for example, groups of ten or twenty struts may all have the same length. The desired result is that the incremental changes are sufficiently small that there is no substantial difference in properties from one group of struts to the next. There are advantages of both approaches: by adjusting the length of each successive pair of struts, the resulting pattern of bridges has smaller dislocations; but, by having groups of pairs of struts of equal length, the design process is simplified, analysis is simplified, and manufacturing inspections are reduced because there is a smaller number of distinctly sized features. There are other alternative embodiments of the expanded tapered stent. For example, groups of strut pairs can be varied in length and width over the length of the taper. In another example, every three strut pairs could have the same dimensions.

A configuration and geometry of bridges is chosen to provide the desired amount of flexibility and integrity. In general, a higher number of bridges provide a stent with greater resistance to deformation and resistance to fatigue and a lower number of bridges provide a stent with less resistance to deformation but increased flexibility.

In a first exemplary embodiment of the present invention, the density of bridges is maintained substantially even over the length of the stent such that there is an approximately equal number of struts disposed between adjacent bridges in all areas of the stent. If the number of struts per turn is maintained constant, and the properties of the stent are varied by some characteristic other than circumferential frequency, the bridge pattern may remain constant along the length of the stent.

In a second exemplary embodiment of the present invention, the pattern of the bridges remains constant along the length of the stent, but the attachment points are adapted to the configuration of the struts, which can vary in length, width, or both.

In a third exemplary embodiment of the present invention, the density of bridges is varied over the length of the stent so that there is a different number of struts disposed between adjacent bridges in different areas of the stent. When the number of struts per turn is varied along the length of the stent, there are discontinuities in the bridge configuration. Accordingly, there is not a constant mapping relationship between the loops of one turn and the loops of the adjacent turns because there would be differing numbers of loops in the adjacent turns. Thus, the bridges are adapted to the struts.

A conventional kerf shape between two struts 10 and a loop 20 is a rectangle with a rounded end as shown, for example, in the left-most turn of FIG. 18 (smaller end 2). The "inside" kerf can be kept small at this hairpin end by forming triangular windows at the hairpin end. Alternatively, the inside hairpin radius can be opened up, making it less likely to crack or break at this point, as illustrated in FIG. 18.

Figure 21:
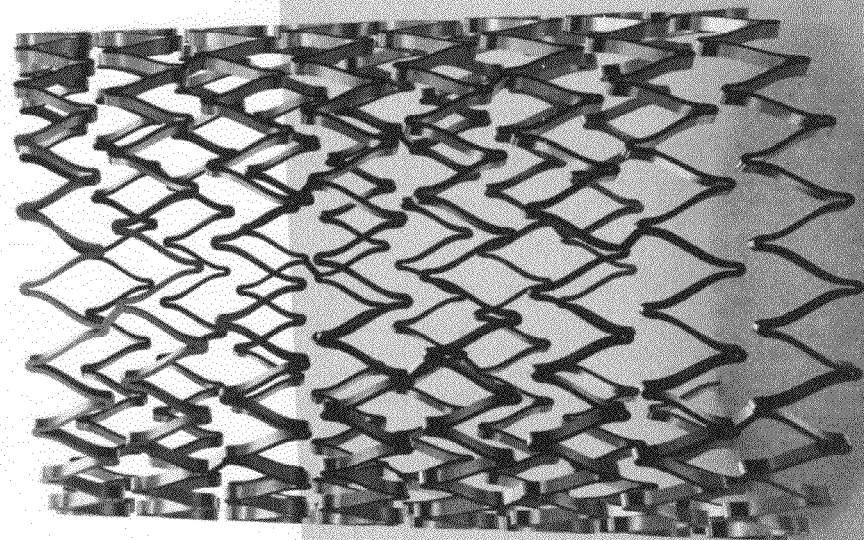
FIG. 21 is a perspective, enlarged, diagrammatic representation of an exemplary configuration of a tapered helical stent according to the invention in an expanded state.
Figure 22:
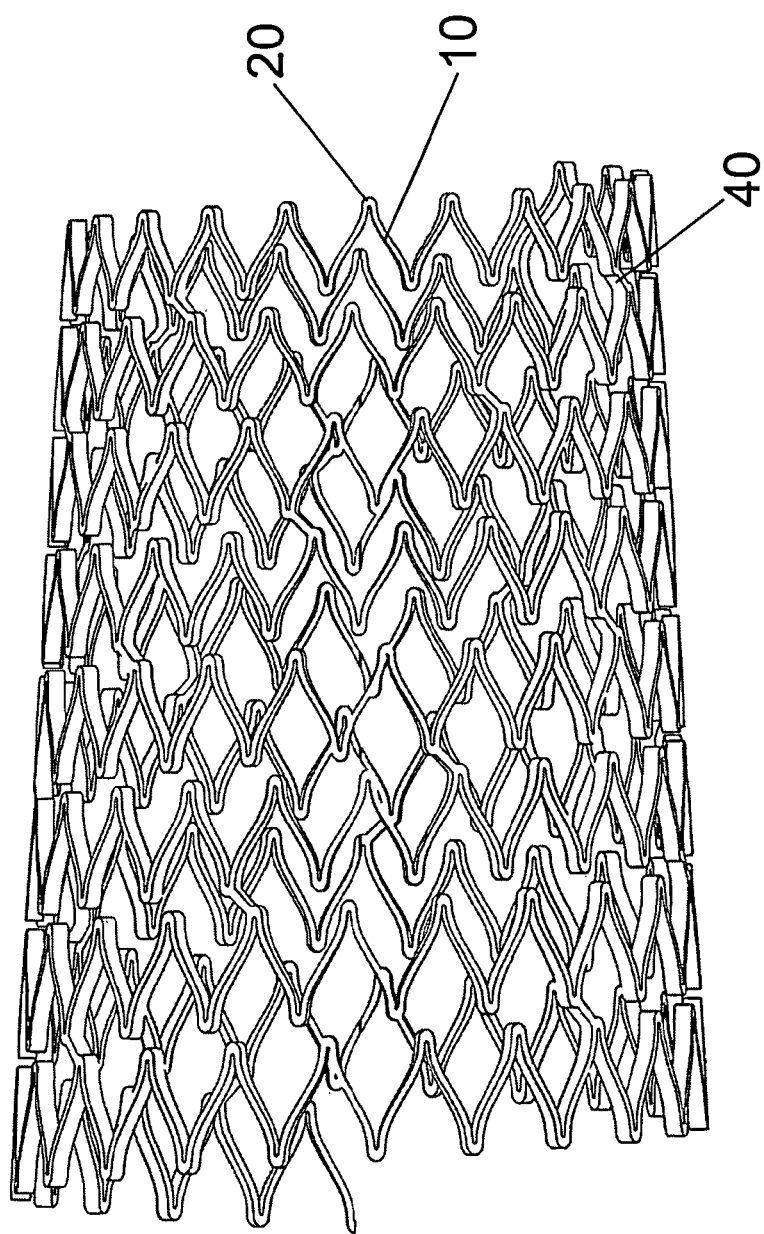
FIG. 22 is an enlarged, side elevational, diagrammatic representation of an exemplary configuration of a tapered helical stent according to the invention in an expanded state.
Figure 23:
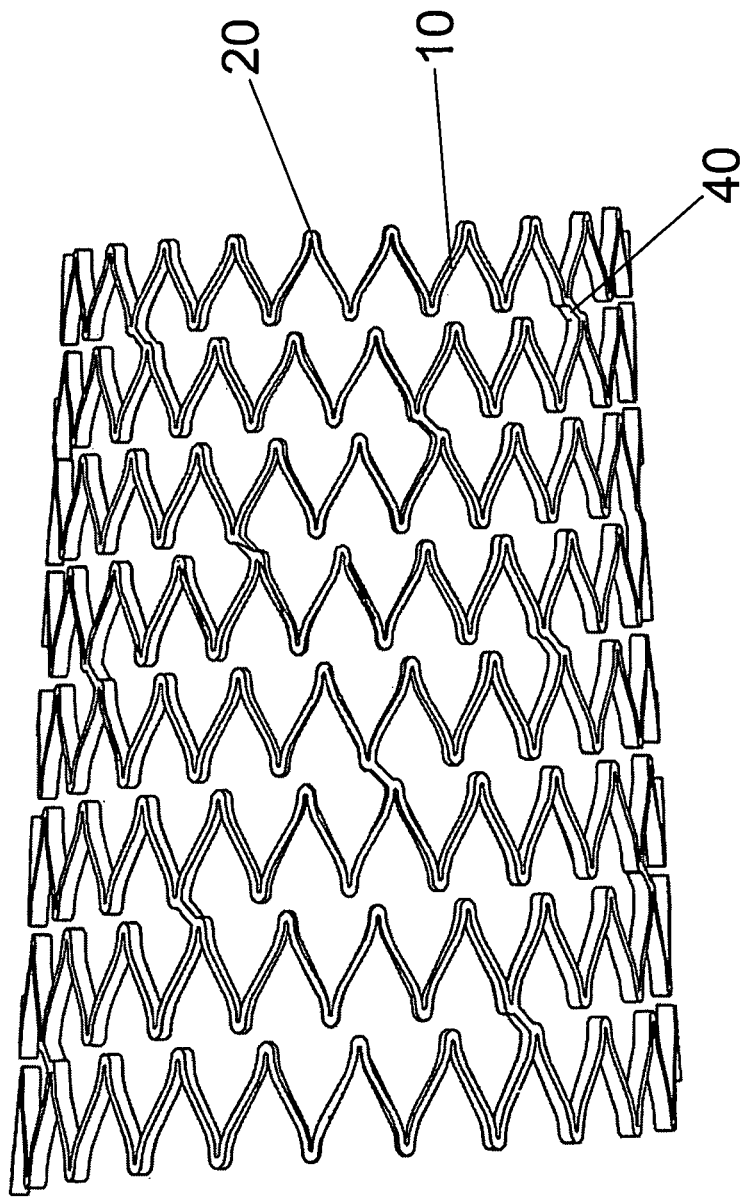
FIG. 23 an enlarged, side elevational, diagrammatic representation of the tapered helical stent of FIG. 22 with the rear half removed.
Figure 24:
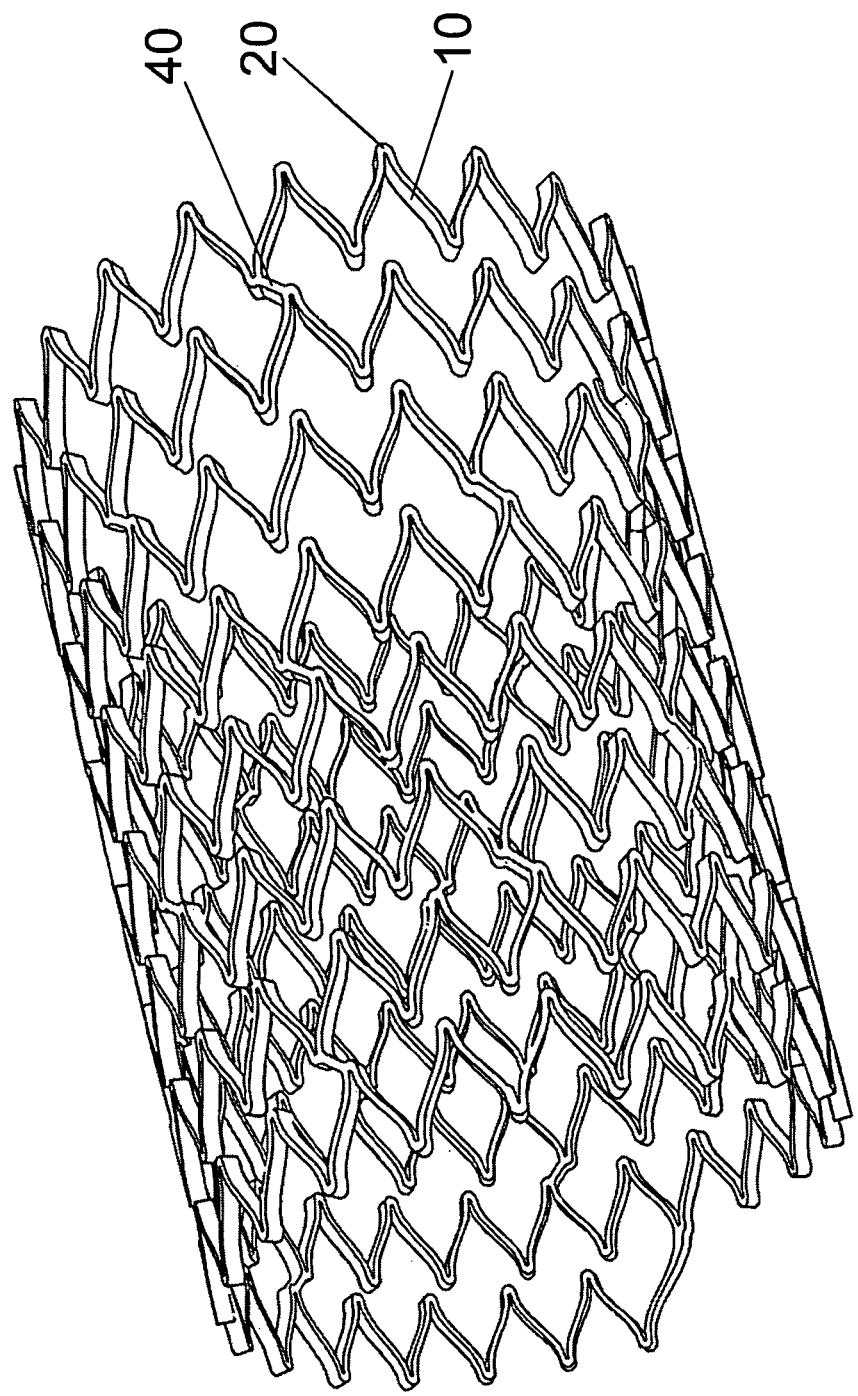
FIG. 24 is an enlarged, perspective, diagrammatic representation of an exemplary configuration of a tapered helical stent according to the invention in an expanded state.
Figure 25:
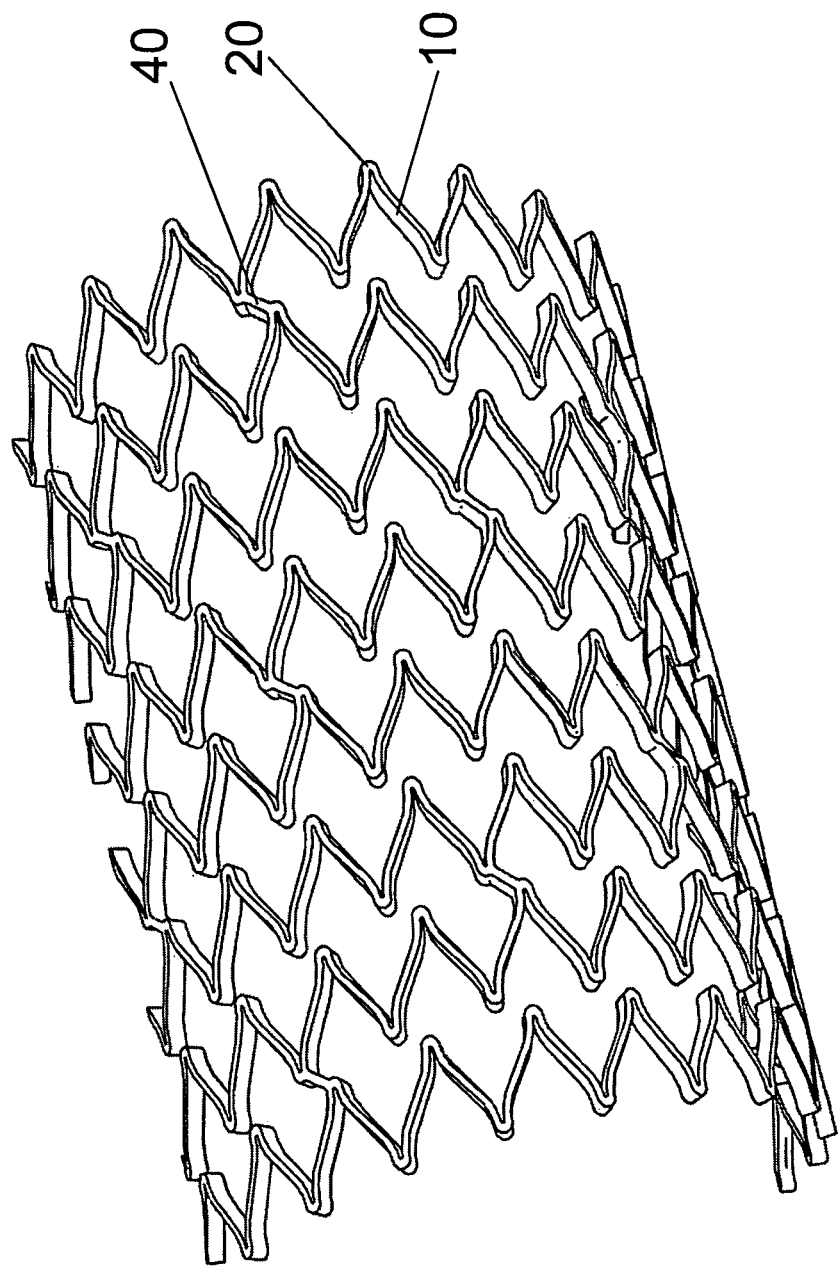
FIG. 25 an enlarged, perspective, diagrammatic representation of the tapered helical stent of FIG. 24 with the rear half removed.

If a stent 1 according to the invention is fully expanded, it may look like the configuration shown in FIG. 21. It is noted that the configuration of FIG. 21 is merely an illustrative representation of a stent according to the invention because, in practice, the change from 6 mm to 8 mm, for example, will be barely perceptible to the naked human eye. Therefore, FIG. 21 has an enhanced configuration that is exaggerated so that features of a stent according to the invention can be explained. A side elevation of such an expanded tapered helical stent 1 is shown in FIG. 22. As can be appreciated, because of the number of struts, it is difficult to differentiate the rear side of the stent 1 from the front side. Accordingly, the rear half of the stent 1 of FIG. 22 has been removed in FIG. 23. An isometric perspective view is shown in FIG. 24 and, like, FIG. 23, the representation in FIG. 25 has the rear half removed for clarity. It is noted that FIGS. 21 to 25 are merely approximate representations of a stent that can be made according to the invention. They are not mathematically accurate and, especially, they are not drawn to scale.

A helical stent according to the present invention having a tapered shape when expanded may be configured as a balloon-expandable stent or as a self-expanding stent. Construction considerations differ for these two applications.

Balloon-expanded stents are not generally configured to provide constant pressure against the vessel wall. However, the expansion of the stent is achieved by pressurizing a balloon, so it is advantageous if the resistance to expansion of the stent at each point along its length is proportional to the intended vessel size. Thus, a balloon expanded by hydrostatic pressure (equal at all points on the balloon surface) will cause the stent to expand to the desired diameter at each point along its length. Even if the stent is tapered, the balloon will still impart the same force at each longitudinal point. For example, a stent configured according to such criterion and intended for a vessel that tapers from 8 mm diameter to 6 mm diameter should expand to these diameters when forced outward by a balloon inflated to the appropriate pressure and such a stent will have a resistance to expansion at each point along its length proportional to the intended vessel size.

Because balloon-expanded stents must be made of malleable material, flexibility must be imparted primarily by inelastic deformation of the struts and the connecting bridges, which must be made slender to minimize the force needed to bend the stent. Flexibility of balloon-expanded stents is primarily of importance during the process of introducing the stent into the anatomy (while it is crimped onto a delivery balloon) and during expansion. Once expanded into the anatomy, the amount of flexibility of a balloon-expanded stent is minimal because of the low yield stress of materials suitable for balloon-expanded stents (e.g., annealed stainless steel, annealed chromium-cobalt alloys, gold, or platinum alloys).

Accordingly, balloon-expanded stents are typically configured with slender struts and connecting bridges. Even when crimped to a small diameter for delivery, there is a significant amount of void space in a balloon-expanded stent. The slender elements, nonetheless, provide substantial rigidity when the stent is expanded because of their high modulus of elasticity (Young's Modulus) and some amount of cold work during expansion that raises the local yield strength. Also, expanded stents typically have cell structures with wider-open angles, which raise the circumferential stress needed to collapse them (the "cosine effect").

In an exemplary embodiment of a tapered helical stent 1 according to the present invention optimized as a balloon-expanded stent (Embodiment $1_{BE}$), the stent 1 is constructed of a malleable alloy (e.g., platinum-5% iridium) having a thickness of 60 microns. The struts 10 have a width equal to 0.1 times the length of the struts 10. In Embodiment $1_{BE}$, the size of the struts 10 is kept proportional to the desired expanded diameter at each station along the stent 1. In this example (a conical or tapered stent), the distal end 3 expands to 4.0 mm diameter and the struts 10 are 2.0 mm in length. At the proximal end 2, which expands to 3.0 mm diameter, the struts are 1.5 mm in length. Along the length of the stent (from the proximal end 2 to the distal end 3), the length of the struts 10 may be varied such that each successive strut pair is incrementally longer. The width of the struts 10 is also varied according to a mathematical relationship with the strut length; in Embodiment $1_{BE}$, the width is maintained proportional to the length of the strut 10. In Embodiment $1_{BE}$, the stent 1 has twelve pairs of struts 10 per helical turn throughout the length of the stent.

The bridge configuration of the tapered helical stent 1 is chosen to provide sufficient integrity during introduction and deployment without adversely affecting the flexibility of the stent 1 once deployed. In Embodiment $1_{BE}$, for example, an array of four bridges 40 per helical turn at the distal (larger) end 3 would decrease in the middle of the stent to three bridges 40 per helical turn.

Balloon-expanded stents 1 according to the present invention may assume a tapered expanded shape either by the application of a varying expansion force over the length of the stent 1 (for example, by pressurization of an asymmetrical balloon, or by successive pressurizations of a balloon at different pressures) or by the application of a uniform expansion force (for example, uniform pressure in a symmetrical balloon) over the length of the stent, or by a combination of these measures. The stent 1 may be configured to expand asymmetrically when expanded by a uniform expansion force (by varying the resistance to expansion of the stent over its length), or the stent 1 may be configured with uniform resistance to expansion, but with the proper structure to provide uniform (or otherwise programmed) properties over the length of the stent 1 when expanded to an asymmetric shape, such as a taper. In one exemplary embodiment, groups of strut pairs can be varied in length and width over the length of the balloon-expanded stent 1. In another exemplary embodiment, groups including three strut pairs could have the same dimensions. As a further example, rather than keeping the same bridge pattern over the length of the balloon-expanded stent 1, the pattern may be varied. In Embodiment $1_{BE}$, for example, rather than having a lower number of bridges 40 at the smaller end 2 of the stent 1, it is possible to have the same bridge configuration (for example, four bridges 40 per helical turn) over the entire length of the stent 1.

In the case of a self-expanding tapered helical stent 1, the stent 1 can be made to generate expansion forces (Chronic Outward Force) and resistance to external forces (Radial Resistive Force) appropriate for the lumen diameter at each segment along its length. Such a tapered helical stent might apply an equal amount of pressure to the lumen wall at every point along its length.

A self-expanding tapered helical stent 1 according to the present invention is made from superelastic material (e.g., Nitinol alloy, gold superelastic alloys, or other nickel and titanium containing superelastic alloys known to those skilled in the art) by laser-machining from a tube. Because of the lower stiffness of superelastic materials, which exert the substantially same force over a wide range of deformations, it is customary to construct self-expanding stents to contain the maximum possible amount of metal, consistent with collapsing the stent for insertion into a delivery system catheter. Accordingly, the struts 10 are made as wide as possible. The stent designer may choose a number of struts 10 per helical turn, making the struts 10 as wide as possible by separating them one from another by the smallest practicable laser-cut kerf. The length of the struts 10 is, then, determined by a mathematical relationship determined by the designer that will assure that the stent 1 can be expanded and collapsed and will be durable when affected by bending, torsion, extension-compression, pinching, pulsatile radial compression-expansion, and other performance requirements.

An exemplary embodiment for a self-expanding tapered helical stent 1 includes a conical shape (being tapered shape when fully expanded) tapering from 8 mm diameter to 6 mm diameter (Embodiment $2_{SE}$). This stent 1 is machined from a tube of Nitinol with an outside diameter of 1.72 mm and a wall thickness of 300 microns. After polishing, the thickness of the stent is approximately 275 microns. The number of struts 10 per revolution is selected to be 36 and constant over the length of the stent 1. The struts 10 vary in length from 2 mm at the larger end 3 to 1.5 mm at the smaller end 2. Strut width, proportional to the length, varies from 110 microns to 80 microns over the length. The pattern of bridges 40 is constant over the length of the stent 1 at six per helical turn.

Self-expanding stents are heat-treated while being held in a certain configuration ("heat setting") so that they have a memorized shape. To achieve a self-expanding stent that has a tapered fully expanded shape according to the present invention, the stent 1 is held in the desired shape (possibly, by placing it onto a tapered tool) and heating it to approximately 450° C. (depending upon the properties of the superelastic material being used) for approximately three minutes. Once cooled, the stent 1 will remain in that shape, and it will recover to that shape if unconstrained after being expressed from its delivery system.

Although Embodiment $2_{SE}$ will recover to a tapered shape if unconstrained, it is possible to make a stent 1 that is heat-set to a non-tapered shape, yet it might assume a tapered shape in a tapered body lumen. For example, a stent 1 can be configured with geometry or other properties varying over its length as would be appropriate for use in a tapered body lumen, yet it might be heat-set to a non-tapered shape to achieve certain desired results, such as reduced outward pressure in the large-diameter segment or for prevention of over-expansion in aneurismal lumina. In either embodiment, groups of strut pairs can be varied in length and width over the length of the tapered self-expanding stent 1. For example, groups of three strut pairs could have the same dimensions. Also, rather than keeping the same bridge pattern over the length of the self-expanding stent, the bridge pattern may be varied. For example, in Embodiment $2_{SE}$, rather than maintain a pattern of six bridges 40 per helical turn, it is possible to configure a lower number of bridges 40 at the smaller end 2 of the stent 1. It should be noted that, although certain bridge patterns repeat uniformly, other bridge patterns are possible. After placing a bridge 40 every three pairs of struts 10 (i.e., six bridges per helical turn in a stent with eighteen pairs of struts 10 per helical turn) at the larger end 3 of the stent 1 (as described in Embodiment $2_{SE}$) it is possible to place bridges closer together at the smaller end 2, for example, every four pairs.

More complicated patterns of bridges may also be chosen; for example, a bridge 40 may be placed four pairs after the first bridge 40, then after five pairs, then after four pairs, then after five pairs, and so forth. It should be appreciated that, in a tapered helical stent configuration, it is not necessary for each turn of the helix to have the same number of bridges 40, nor does there need to be a repeating pattern of bridges 40 from turn to turn.

The stent 1 according to the invention, in any of the embodiments set forth above (whether self-expanding or balloon expanded), is not limited to changing the strut length, the strut width, or the kerf. The struts 10, loops 20, and bridges 40 can be varied by other measures. First, the thickness of the struts 10, loops 20, and bridges 40 may be varied over the length of the stent 1 to generate a tapered stent shape when expanded. Such a stent can be produced by laser-machining the desired pattern into a tube that has wall thickness varying from one end to the other; such a variable wall thickness can be achieved by honing a tapered bore into a tube or by grinding or polishing the outer surface of the tube to remove more wall thickness at one end than the other. For example, the wall thickness of 275 microns at one end of the stent may be reduced to 200 microns at the opposite end. Second, the material from which any part of the stent 1 is made (struts 10, loops 20, bridges 40) may be varied over the length of the stent 1 to generate the tapered shape when the stent 1 is expanded., as might be achieved by heat-treating, ion-implanting, or alloying one end of the tube differently than the other. Third, by applying coatings, platings, or attachments by such measures as mechanical attachment, welding, brazing, soldering, adhesion, bonding, polymerization, solvent casting, thermal deposition, fasteners, and press fits, physical properties of the stent 1 may be varied over the length of the stent 1 to provide different characteristics in different locations. By varying the local properties of the stent 1 by any of these measures along its length, the stent 1 can be made to have a tapered expanded shape.

The tapered helical stent 1 of the present invention may be constructed so that there is a smooth or gradual incremental progression of properties from one end of the stent 1 to the other, even though there may not be a conical or tapered shape to the stent 1, either in the compressed or expanded condition (that is, either freely-expanded in the case of a self-expanding stent, or after unconstrained expansion by a cylindrical balloon in the case of a balloon-expanded stent). These gradually incremental or smoothly changing properties may be achieved by any of the variations (or by combinations thereof) including thickness, metallurgical properties, and/or materials. Similarly, for such an embodiment, groups of strut pairs can be varied in length and width over the length of the taper. For example, every three, four, or five strut pairs could have the same dimensions. Also, rather than keeping the same bridge pattern over the length of the stent, the bridge pattern may be varied.

There are a number of criteria that can influence the design of tapered helical stents 1 according to the present invention. One such design criterion includes maintaining a proportional strut width. To provide similar properties along the length of a tapered helical stent 1 (that is, a stent intended for use in a tapered body lumen), and to maintain the durability (under cyclic flexion and compression) of the stent over its entire length, it is desirable to maintain a certain mathematical relationship between the length and width of such features as the struts 10, loops 20, and bridges 40. In exemplary embodiments, maintaining linear proportionality for the dimensions of these features is desired, although more complex mathematical relationships may be used, such as proportionality to the square root, third root, or 3/2 root, geometrically, or exponentially depending upon the primary design constraints for stent performance and durability.

Another design criterion is maintaining a uniform opening angle. To provide similar expansion characteristics, and to control the opening sizes and material strains, it may be desired to maintain uniform opening angles between struts of a pair. Because quality inspection of stents may be expensive and time-consuming, providing easily inspected features, such as uniform expansion angles, may be of benefit.

Still another design criterion is the maintenance of uniform maximum crimp strains. In the design of self-expanding stents, it is important to make certain that the maximum strains at any point on the stent does not exceed a specified level during compression of the stent into its delivery system. Typical values for this limit are 6% to 8%.

Other characteristics of stents 1 according to the present invention relate to the longitudinal pressure profile. A first exemplary profile is uniform pressure. It is usually considered beneficial and preferred to apply a uniform amount of contact pressure to the body lumen being stented. When the number of struts per unit length and their dimensions are varied in a progressive manner, the properties at each point along the length of the stent may be made appropriate for the local diameter of the stent (and, hence, the stented lumen) when the stent is expanded. Therefore, an exemplary embodiment of the present invention has geometry and material properties that assure even pressure along all segments of the tapered or otherwise varying body lumen to be stented. However, it is also possible to adopt other criteria, such as contact pressure in proportion to diameter, higher contact pressures in the middle segment of the stent, higher contact pressures at the distal and/or proximal ends, and so forth. Another pressure profile example includes gradients in the contact pressure. In some of the embodiments presented, the properties of the stent 1 and/or its geometry are configured to be graded linearly (that is to say, in a proportional way) along the length of the stent. It is also possible to provide, using the same methods, shape and/or properties that vary in non-linear ways along the length of the stent. For example, the properties might be constant over certain parts of the distal and proximal ends of the stent, yet may vary over a middle segment. Proportionalities other than linear (first-order) are also possible, such as parabolic (second-order), cubic (third-order), or any other arbitrary relationship.

Some of the helical stent geometries described herein have been of the type where alternating struts 10 are slightly longer and slightly shorter, so that the serpentine winding advances helically while the struts 10 maintain substantially a longitudinal alignment in the non-expanded shape. Other configurations are possible, such as that taught by Corso, where the helical serpentine advances with equal-length struts; in such a configuration, the struts 10 are approximately perpendicular to the helical axis when unexpanded.

Some of the foregoing embodiments describe alternative locations for the bridges 40 that connect adjacent helical turns of the stent. The shape of the bridges 40 may be varied from those shown and may be longitudinal, circumferential, or may be oriented in a diagonal or helical direction. In addition, bridges 40 may cross the space between the adjacent helical turns such that they join loops immediately next to one another, loops displaced from one another, nested loops (hill-to-valley), and/or abutting loops (hill-to-hill). In addition, other configurations are possible and known to those skilled in the art, such as valley-to-valley (where the connecting bridge 40 transits between the struts of a pair to reach the connecting loop at the opposite end). Exemplary bridges 40 may be straight, curved, curvilinear, spiral, sinusoidal, or of any other arbitrary shape.

At the proximal and distal ends 2, 3 of the tapered helical stent 1 it is possible, and in some instances desired, to provide features that extend axially beyond the helical portion of the stent 1. In particular, tabs, extensions, lollipops, or paddle-shaped extensions may be provided to assist in deployment and anchoring of the stent 1 in the body lumen. These features may be smooth or may be equipped with engaging features such as barbs, prongs, or needles.

With respect to marking the stent 1 according to the present invention, any number of prior art systems can be used. For example, fiducial markers visible under X-ray, MRI, ultrasound, and/or other imaging measures can be used. Some specific marker configurations are particularly suitable for stents to be used in tapered body lumina, such as a single distal marker. In the special case of a stent for use in the carotid artery, and for other uses as well, a single marker placed at the distal end of the stent 1 is all that can be required for precise stent placement, and, by eliminating redundant markers at the distal end or any markers at the proximal end, the area of the stent is limited so that non-diseased areas are not impinged upon by features of the stent.

In the present invention of a tapered helical stent, a particularly advantageous location for a single marker is at the notch which naturally occurs at the termination of the helical serpentine winding. A single marker placed at that location allows precise positioning during delivery while eliminating unwanted intrusion of portions of the stent into areas that are not desired to be treated. Alternatively, the marker may be placed in, on, or otherwise made a part of or attached to a paddle, tab, or lollipop-shaped extension of the stent at this location.

As described above for distal markers, it is possible to place a single marker in the helical notch at the proximal end of the stent. While not all practitioners desire a proximal marker, some do. Placing a marker in this position has an additional advantage of evening out the proximal end 2 of the helical stent, which facilitates application of the pushing-out force needed to express a self-expanding stent 1 from its delivery system. Even if a proximal marker is not desired, it may be advantageous to provide a similar feature in the helical notch at the proximal end to facilitate delivery of a self-expanding stent 1 or to make the proximal end 2 of a balloon-expandable stent more even than would be possible without the marker.

In addition to those described here, other markers, multiple markers, or markers at other locations on the tapered stent 1 are possible and may be advantageous in certain circumstances, as when positioning the stent 1 relative to a bifurcation, branch lumen, or other anatomical feature.

In addition to the overall tapered shape (either intrinsic to the stent or caused by its placement in a tapered body lumen) of the present invention, it may be preferable and advantageous to flare the proximal end 2, the distal end 3, or both ends 2, 3 of the stent 1 to aid in deployment and anchoring. The flared shape may be created by a heat-set shape (in the case of a self-expanding stent) or by the action of the expanding balloon upon features at the ends of the stent (in the case of a balloon-expandable stent).

There are different ways to manufacture the tapered stent according to the invention. One exemplary method can include the following steps:

1. A tube of nitinol alloy is provided with a diameter of 1.800 millimeters, a wall thickness of 300 microns, and a length of 60 millimeters;
2. The tube is mounted into a laser-machining station, which has been programmed to make a pattern of kerfs (cuts) of the intended design;
3. The tube is rotated and translated in the laser-machining station relative to the focal spot of the laser so that the intended pattern of kerfs is cut through the wall of the tubing;
4. The cut tube is removed from the laser-machining station;
5. The tube is processed by mechanical and/or chemical measures to remove dross, burrs, spatter, or other excess material from the inside and outside surfaces;
6. The cut and deburred tubing is thoroughly cleaned;
7. The cleaned part is pushed onto a mandrel (by a tapered introducer), which has a diameter slightly larger than the original internal diameter of the tubing (for example, 2.500 millimeters) to expand the part (cut tubing);
8. The mandrel and expanded part are heated to a heat-setting temperature (for example, 540° Celsius) for one minute;
9. The mandrel and expanded heated part are cooled to room temperature;
10. The cooled part is removed from the mandrel and pushed onto a larger mandrel;
11. The larger mandrel and cooled part are, again, heated to a heat-setting temperature for one minute;
12. Steps 9 through 11 are repeated until the part is expanded to slightly less than the final desired diameter of the small end of the finished stent, which can be referred to as a pre-form;
13. The pre-form is pushed onto a conical mandrel to expand one end more than the other end;
14. The heating and cooling steps are performed (as described previously in steps 8 and 9);
15. The conical pre-form is placed onto succeedingly larger (or more-tapered) mandrels, and the heat-treating and cooling steps are repeated until the final expanded conical shape is achieved, which part can be referred to as the unfinished stent;
16. The unfinished stent is removed from the mandrel;

17. The unfinished stent is cleaned and polished by chemical, electrochemical, mechanical, or a combination of processes to produce the desired final surface finish on the finished stent;
18. The finished stent is inspected and cleaned as needed;
19. The finished stent is compressed (at room temperature or at a lower temperature) to a diameter sufficiently small that it can be placed into the delivery system catheter;
20. The stent is placed into the delivery system catheter; and
21. The delivery system and stent are packaged and sterilized.

Although the examples illustrated herein are indicated as being made by laser-machining, it is possible to make the stent of the present invention by other measures, such as electro-discharge machining (EDM), photo-chemical machining (PCM), stamping, conventional machining, chemical deposition (for example, plating), physical vapor deposition (PVD), chemical vapor deposition (CVD), or other measures known to those skilled in the art.

In the foregoing examples, the stent 1 can be made from uniform-diameter tubing (with possibly changing wall thickness) or from tapered-diameter tubing. It is also possible to make the tapered helical stent 1 from tubing with a tapered outer diameter. It is, in fact, particularly advantageous to do so because a stent 1 constructed according to the present invention naturally may have different geometry at opposite ends of the stent. For example, it may be advantageous, as previously described, to have a larger number of struts 10 per helical turn at the larger end 3 of the stent 1.

While stents are customarily machined from constant-outside-diameter tubing, it is possible to machine the stent 1 of the present invention from tapered tubing, so that the end requiring more struts 10 has more circumference out of which to machine those struts 10. Particularly in the case of self-expanding embodiments, where it is common to construct stents according to the criterion of "maximum metal" (that is, removing the smallest possible amount of metal from the stent tubing to make the stent), machining a tapered stent 1 from tapered tubing would allow the design to be optimized at both ends of the stent 1, allowing for the minimum amount of material to be removed at all points along the stent 1.

When machining a self-expanding stent 1 from tapered tubing, it is advantageous to provide reduced wall thickness at the larger end of the tubing to ease compression of the stent 1 into its delivery system.

There are certain considerations that can be discussed with respect to the process for expanding the tapered stent 1 according to the present invention.

Self-expanding stents are expanded by many measures known to those skilled in the art, including the use of tapered mandrels or other internally-expanding tooling. The expansion is usually accomplished in a step-wise fashion, expanding by small increments and heat-treating after each step, in order to minimize the chance of damage to the stent.

In the case of self-expanding helical stents 1 having a tapered shape when freely expanded, in one exemplary process, at least the final heat-setting step will utilize a tapered mandrel or tool to hold the stent 1 in the desired shape during heat treatment.

In the case of self-expanding helical stents 1 that do not have a tapered shape when freely expanded, the final expansion and heat-setting step will be done, for example, with a non-tapered mandrel or tool. However, it may be advantageous to use tapered tools during a portion of the expansion process so that the desired configuration of the stent 1 will be achieved when deployed in a tapered body lumen.

Balloon-expandable stents are typically machined in an intermediate configuration part way between a fully expanded shape and a fully crimped shape. Once machined, such stents must be expanded partially to place them onto the balloon deployment system, after which they are, typically, crimped to hold them onto the balloon during deployment. Many different measures are known to those skilled in the art to crimp, attach, and fix such stents onto balloons. These measures can be used to create a balloon-expandable tapered helical stent 1.

Once completed, stents are customarily polished by a combination of chemical and physical measures. In the case of self-expanding stents, such steps generally include honing, abrasive or bead blasting, acid pickling, mechanical polishing, electropolishing, and passivation. In the case of balloon-expanded stents, similar steps are employed, depending upon the material from which the stent is made. These processes can also be used to create the tapered helical stent 1 according to the present invention.

The invention claimed is:

1. A tapered helical implantation device for peripheral arteries and other body lumina of locally varying diameter, comprising:
    struts connected by loops and shaped in a helical winding, said helical winding defining turns and, when expanded, having a first end with a first expanded circumference, and a second end with a second expanded circumference greater than said first expanded circumference to form a stent tapering outward from said first end towards said second end;
    bridges connecting adjacent ones of said turns; and
    said struts, said loops, and said bridges defining a series of pores aligned along said helix, said pores having a substantially uniform pore size from said first end to said second end even when a diameter of the stent varies along its length from said first end to said second end to form the outwardly tapered stent from said first end to said second end when expanded.

2. The device according to claim 1, wherein said pores have a substantially similar area.

3. The device according to claim 1, wherein said pore size limits a size of a particle that can pass therethrough.

4. The device according to claim 1, wherein said pore size limits a size of a spherical particle that can pass therethrough.

5. The device according to claim 1, wherein:
    said winding defines a longitudinal axis of said stent and an axis of said helical winding; and
    said struts extend one of:
        longitudinally along said longitudinal axis; and
        perpendicular to said axis of said helical winding.

6. The device according to claim 1, wherein said bridges connect adjacent loops on adjacent ones of said turns.

7. The device according to claim 1, wherein said bridges are placed at locations on said helix corresponding to at least one of every third strut pair, every fifth strut pair, and every seventh strut pair.

8. The device according to claim 1, wherein said bridges are disposed in a 5-up-and-5-down pattern.

9. The device according to claim 1, wherein said bridges are disposed in a 5-up-and-7-down pattern.

10. The device according to claim 1, wherein:
    said stent has an overall length; and
    a number of said struts per one of said turns remains the same throughout said overall length.

11. The device according to claim 1, wherein:
said stent has an overall length; and
said struts increase in one of width and length from said first end to said second end at least one of in steps, by linear proportion, and by geometric proportion.

12. The device according to claim 1, wherein:
said stent has an overall length;
said struts of each of said turns have the same size; and
said struts increase in size from one of said turns to another of said turns from said first end to said second end at least one of in steps, by linear proportion, and by geometric proportion.

13. The device according to claim 1, wherein:
said stent has an overall length; and
a density of said bridges is substantially even over said overall length to have an equal number of said struts disposed between adjacent bridges in all areas of said stent.

14. The device according to claim 13, wherein a number of said struts per one of said turns is constant and a pattern of said bridges remains constant along said overall length.

15. The device according to claim 1, wherein:
said stent has an overall length; and
a density of said bridges is varied over said overall length to have a different number of said struts disposed between adjacent ones of said bridges in different areas of said stent.

16. The device according to claim 1, wherein a circumferential distance between ends of said struts at said second end are substantially the same as a circumferential distance between ends of said struts at said first end to create said substantially uniform pore size.

17. The device according to claim 1, wherein a number of said struts at said second end is proportionally larger than a number of said struts at said first end.

18. The device according to claim 1, wherein said stent has a length and, when expanded and placed in a lumen, provides a constant hoop force over said length against the lumen.

19. The device according to claim 1, wherein said stent has a constant metal ratio from said first end to said second end.

20. The device according to claim 1, wherein said first end has a diameter between approximately 4 mm and approximately 6 mm and said second end has a diameter between approximately 6 mm and approximately 10 mm.

21. The device according to claim 1, wherein the lumen is one of a carotid artery, a common bile duct, and a location where an iliac artery joins a superficial femoral artery.

22. The device according to claim 1, wherein said stent is a balloon-expanded stent and has a resistance to expansion at each point along a length of said stent proportional to an intended vessel size in which said stent is to be implanted.

23. The device according to claim 1, wherein said struts and said loops define a kerf having a width, said width of said kerf between said struts defines said width of said struts, and said kerf is varied along said stent to create a taper of said stent when expanded.

24. The device according to claim 1, wherein:
said struts and said loops define a kerf;
said stent has an overall length;
a width of said struts remains constant throughout said overall length;
a width of said kerf between said struts remains constant throughout said overall length;
a number of struts per one of said turns stays the same along an entirety of said overall length; and
said length of said struts varies from said smaller end to said larger end.

25. The device according to claim 1, wherein:
said struts and said loops define a kerf;
said stent has an overall length;
both said width and said length of said struts transition in a constantly increasing manner from said smaller end of said stent to said larger end;
said kerf transitions in a constantly decreasing manner from said smaller end to said larger end; and
a number of said struts per one of said turns remains the same along an entirety of said overall length.

26. The device according to claim 1, wherein:
said struts and said loops define a kerf;
said stent has an overall length;
both said width and said length of said struts transition in a constantly increasing manner from said smaller end to said larger end;
said kerf remains constant throughout said overall length; and
a number of said struts per one of said turns decreases along said overall length from said smaller end to said larger end.

27. The device according to claim 1, wherein:
said stent has an overall length; and
said length and said width of said struts and a count of said struts varies along said overall length to have a number of said struts at said smaller end be larger than a number of said struts at said larger end.

28. The device according to claim 1, wherein:
said stent has an overall length; and
said stent is a tapered balloon-expanded stent and has a resistance to expansion at each point along said overall length proportional to an intended implantation vessel size.

29. The device according to claim 1, wherein said struts and said loops are shaped to expand asymmetrically when said stent is expanded by a uniform expansion force.

30. The device according to claim 29, wherein said stent has a uniform resistance to expansion and has uniform expansion properties over said overall length when expanded to an asymmetric shape.

31. The device according to claim 1, wherein:
said stent has an overall length; and
said stent is a self-expanding tapered helical stent and generates expansion forces and resistance to external forces proportional to an adjacent lumen diameter at each point along said overall length to apply a substantially equal pressure to an implantation lumen wall at every point along said overall length.

32. The device according to claim 1, wherein:
said stent has an overall length; and
an opening angle between struts of a pair of said struts is uniform over said overall length.

33. A tapered helical implantation device for peripheral arteries and other body lumina of locally varying diameter, comprising:
a helical winding of struts connected by loops, said helical winding defining a first end, a second end, and helical turns;
said struts each having a length and a width, at least one of:
said length of said struts;
said width of said struts; and
a frequency of said struts per one of said turns,
being varied from said first end to said second end to form a diameter-varying implantable stent outwardly tapered from said first end to said second end when expanded;
bridges connecting adjacent ones of said turns; and said struts, said loops, and said bridges defining a series of pores aligned along said helix, said pores having a substantially uniform pore size from said first end to said second end even when a diameter of the stent varies along its length from said first end to said second end to form the diameter-varying stent outwardly tapered from said first end to said second end when expanded.

34. An implantation device for lumina of locally varying diameter, comprising:
  a helical winding defining turns and, when expanded, having a first end with a first expanded circumference and a second end with a second expanded circumference greater than said first expanded circumference to form a stent tapering outward from said first end towards said second end;
  bridges connecting adjacent ones of said turns; and
  said winding and said bridges defining a series of pores aligned along said helix, said pores having a substantially uniform pore size from said first end to said second end even when a diameter of the stent varies along its length from said first end to said second end to form the outwardly tapered stent from said first end to said second end when expanded.

35. A tapered helical implantation device for peripheral arteries and other body lumina of locally varying diameter, comprising:
  struts connected by loops and shaped in a helical winding, said helical winding defining turns and, when expanded, having a first end with a first expanded circumference, and a second end with a second expanded circumference greater than said first expanded circumference to form a stent tapering outward from said first end towards said second end;
  bridges connecting adjacent ones of said turns; and
  said struts, said loops, and said bridges defining a series of pores aligned along said helix, said pores being shaped to permit particles no greater than a given size to pass therethrough, said given size being substantially constant from said first end to said second end even when a diameter of the stent varies along its length from said first end to said second end to form the outwardly tapered stent from said first end to said second end when expanded.

36. A tapered helical implantation device for peripheral arteries and other body lumina of locally varying diameter, comprising:
  a helical winding of struts connected by loops, said helical winding defining a first end, a second end, and helical turns;
  said struts each having a length and a width, at least one of:
    said length of said struts;
    said width of said struts; and
    a frequency of said struts per one of said turns,
  being varied from said first end to said second end to form a diameter-varying implantable stent outwardly tapered from said first end to said second end when expanded;
  bridges connecting adjacent ones of said turns; and
  said struts, said loops, and said bridges defining a series of pores aligned along said helix, said pores being shaped to permit particles no greater than a given size to pass therethrough, said given size being substantially constant from said first end to said second end even when a diameter of the stent varies along its length from said first end to said second end to form the diameter-varying stent outwardly tapered from said first end to said second end when expanded.

37. A tapered helical implantation device for peripheral arteries and other body lumina of locally varying diameter, comprising:
  metal struts connected by metal loops and shaped in a helical winding, said helical winding defining turns and, when expanded, having a first end with a first expanded circumference, and a second end with a second expanded circumference greater than said first expanded circumference to form a stent tapering outward from said first end towards said second end;
  said first end having a first end turn and said second end having a second end turn;
  metal bridges connecting adjacent ones of said turns;
  said struts, said loops, and said bridges between said first and second end turns having a substantially constant metal-to-total area proportion; and
  said winding and said bridges defining a series of pores aligned along said helix, said pores having a substantially uniform pore size from said first end to said second end even when a diameter of the stent varies along its length from said first end to said second end to form the outwardly tapered stent from said first end to said second end when expanded.

38. A tapered helical implantation device for peripheral arteries and other body lumina of locally varying diameter, comprising:
  a helical winding of struts connected by loops, said helical winding defining a first end, a second end, and helical turns;
  said first end having a first end turn and said second end having a second end turn;
  said struts each having a length and a width, at least one of:
    said length of said struts;
    said width of said struts; and
    a frequency of said struts per one of said turns,
  being varied from said first end to said second end to form a diameter-varying implantable stent outwardly tapered from said first end to said second end when expanded;
  bridges connecting adjacent ones of said turns;
  said struts, said loops, and said bridges between said first and second end turns having a substantially constant metal-to-total area proportion; and
  said struts, said loops, and said bridges defining a series of pores aligned along said helix, said pores being shaped to permit particles no greater than a given size to pass therethrough, said given size being substantially constant from said first end to said second end even when a diameter of the stent varies along its length from said first end to said second end to form the diameter-varying stent outwardly tapered from said first end to said second end when expanded.

* * * * *